United States Patent
Funk et al.

(10) Patent No.: US 6,667,176 B1
(45) Date of Patent: Dec. 23, 2003

(54) CDNA LIBRARIES REFLECTING GENE EXPRESSION DURING GROWTH AND DIFFERENTIATION OF HUMAN PLURIPOTENT STEM CELLS

(75) Inventors: Walter D. Funk, Hayward, CA (US); Melissa K. Carpenter, Foster City, CA (US); Joseph D. Gold, San Francisco, CA (US); Margaret S. Inokuma, San Jose, CA (US); Chunhui Xu, Cupertino, CA (US)

(73) Assignee: Geron Corporation, Menlo Park, CA (US)

(*) Notice: Subject to any disclaimer, the term of this patent is extended or adjusted under 35 U.S.C. 154(b) by 0 days.

(21) Appl. No.: 09/688,031

(22) Filed: Oct. 10, 2000

Related U.S. Application Data

(60) Provisional application No. 60/220,064, filed on Jul. 21, 2000, provisional application No. 60/216,387, filed on Jul. 7, 2000, provisional application No. 60/213,739, filed on Jun. 22, 2000, provisional application No. 60/213,740, filed on Jun. 22, 2000, and provisional application No. 60/175,581, filed on Jan. 11, 2000.

(51) Int. Cl.$^7$ .................................................. C12N 5/06
(52) U.S. Cl. ........................ 435/363; 435/366; 435/377; 435/320.1; 536/23.1
(58) Field of Search .......................... 435/6, 320.1, 325, 435/455, 363, 366, 377; 536/23.1

(56) References Cited

U.S. PATENT DOCUMENTS

| | | | | |
|---|---|---|---|---|
| 4,829,000 A | * | 5/1989 | Kleinman et al. | 435/240.23 |
| 5,104,795 A | | 4/1992 | Lee et al. | 435/69.1 |
| 5,166,065 A | | 11/1992 | Williams et al. | 435/240.1 |
| 5,234,809 A | | 8/1993 | Boom et al. | 435/91 |
| 5,332,672 A | | 7/1994 | Conover et al. | 435/240.2 |
| 5,405,772 A | | 4/1995 | Ponting | 435/240.31 |
| 5,453,357 A | | 9/1995 | Hogan | 435/7.21 |
| 5,523,226 A | | 6/1996 | Wheeler | 435/240.2 |
| 5,583,016 A | | 12/1996 | Villeponteau et al. | 435/91.3 |
| 5,635,387 A | * | 6/1997 | Fei et al. | 435/378 |
| 5,639,618 A | | 6/1997 | Gay | 435/7.21 |
| 5,643,761 A | | 7/1997 | Fisher et al. | 435/91.1 |
| 5,672,499 A | | 9/1997 | Anderson et al. | 435/240.4 |
| 5,789,158 A | | 8/1998 | Knowles et al. | 435/6 |
| 5,840,484 A | | 11/1998 | Seilhamer et al. | 435/6 |
| 5,843,780 A | | 12/1998 | Thomson | 435/363 |
| 5,856,136 A | | 1/1999 | Au-Young | 435/69.3 |
| 5,914,268 A | | 6/1999 | Keller et al. | 435/325 |
| 5,922,597 A | | 7/1999 | Verfaillie et al. | 435/372.1 |
| 5,942,435 A | | 8/1999 | Wheeler | 435/325 |
| 5,968,829 A | | 10/1999 | Carpenter | 435/467 |
| 5,981,165 A | | 11/1999 | Weiss et al. | 435/4 |
| 6,040,180 A | | 3/2000 | Johe | 435/377 |
| 6,261,556 B1 | | 7/2001 | Weinrich et al. | 424/94.5 |

FOREIGN PATENT DOCUMENTS

| | | |
|---|---|---|
| EP | 0695351 B1 | 2/1996 |
| EP | 0695 351 B1 | 12/1999 |
| FR | 2744133 | 8/1997 |
| WO | WO 94/07997 | 4/1994 |
| WO | WO 96/17627 | 6/1996 |
| WO | WO 97/21802 | 6/1997 |
| WO | WO 97/28253 | 8/1997 |
| WO | WO 97/30151 | 8/1997 |
| WO | WO 97/47734 | 12/1997 |
| WO | WO 98/00540 | 1/1998 |
| WO | WO 98/30679 | 7/1998 |
| WO | WO 98/43679 | 10/1998 |
| WO | WO 99/01552 | 1/1999 |
| WO | WO 99/10535 | 3/1999 |
| WO | WO 99/20741 | 4/1999 |
| WO | WO 99/42122 | 8/1999 |
| WO | WO 99/43785 | 9/1999 |
| WO | WO 99/10535 | 3/2000 |

OTHER PUBLICATIONS

Thomson et.al.; Isolation of a primate embryonic stem cell line, 1995, Proc. Natl. Acad. Sci., vol. 92: 7844–7848.*

Lu et.al.; Retrovirus–Mediated Gene Expression in Hematopoietic Cells Correlates Inversely with Growth Factor Stimulation, 1996, Human Gene Therapy 7: 2263–2271.*

Mao et.al.; Identification of genes expressed in human CD34+ hematopoietic stem progenitor cells by expressed sequences tags and efficient full–length cDNA cloning, 1998, Proc. Natl. Acad. Sci., vol. 95: 8175–8180.*

Fabb, SA, et al., High– efficiency human B–cell cloning using hygromycin B–resistant feeder cells, Biotechniques 22:814 (1997).

Amit, M., et al., "Clonally Derived Human Embryonic Stem Cell Lines Maintain Pluripotency and Proliferative Potential for Prolonged Periods of Culture," Dev. Biology, 227:000 (2000).

Andrews, P., "Retinoic Acid Induces Neuronal Differentiation of a Cloned Human Embryonal Carcinoma Cell Line in Vitro," Dev. Biol., 103:285 (1984).

Brook, F., et al., "The Origin and Efficient Dirivation of Embryonic Stem Cells in the Mouse," Proc. Natl. Acad. Sci., 94:5709 (1997).

(List continued on next page.)

Primary Examiner—Deborah Crouch
Assistant Examiner—Thai-An N. Ton
(74) Attorney, Agent, or Firm—J. Michael Schiff; David J. Earp

(57) ABSTRACT

This disclosure provides a system for obtaining expression libraries from primate pluripotent stem (pPS) cells. pPS cells can be maintained in vitro without requiring a layer of feeder cells to inhibit differentiation. The role of the feeder cells is replaced by several other culture conditions provided in a suitable combination. Conditions that promote pPS cell growth without differentiation include supporting the culture on an extracellular matrix, and culturing the cells in a medium conditioned by another cell type. The cDNA libraries from such cultures are devoid of transcripts of feeder cell origin, relatively uncontaminated by transcripts from differentiated cells, and can have a high proportion of full-length transcripts. Subtraction libraries can also be produced that are enriched for transcripts modulated during differentiation.

27 Claims, 10 Drawing Sheets

OTHER PUBLICATIONS

Carnegie, J., "Immonolocalization of Fibronectin and Laminin Within Rat Blastocysts Cultured Under Serum–Free Conditions," J. Reprod. Fert., 91:423 (1991).

Carninci, P., et al., "High–Efficiency Full–Length cDNA Cloning," Methods Enzymol., 303:19 (1999).

Eisen, M., "Cluster Analysis and Display of Genome–wide Expression Patturns," Proc. Natl. Acad. Sci., 95:14868 (1998).

Elges, R., et al., "Establishment of Human Embryonic Stem Cell–Transfected Clones Carrying a Marker for Undifferentiated Cells," Curr. Biol., 11:514 (2001).

Fenderson, B., et al., "Carbohydrate Antigens of Embryonal Carcinoma Cells: Changes Upon Differentiation," APMIS Suppl. 27, 100:109 (1992).

Finley, M., et al., "Synapse Formation and Establishment of Neuronal Polarity by P19 Embryonic Carcinoma Cells and Embryonic Stem Cells," J. Neuroscience, 16:1056 (1996).

Matsuda, T., et al., "STAT3 Activation is Sufficient to Maintain an Undifferentiated State of Mouse Embryonic Stem Cells," EMBO J., 18:4261 (1999).

Pera, M., "Human Pluripotent Stem Cells: a Progress Report," Curr. Opin. Genet. Dev., 11:595 (2001).

Rehman, N., et al., "Development of IVM–IVF Produced 8–Cell Bovine Embyrons in Simple, Serum–Free Media After Conditioning or Co–Culture With Buffalo Rat Liver Cells," Mol. Repro. Dev., 38:251 (1994).

Smith, A., et al., "Inhibition of Pluripotential Embryonic Stem Cell Differentiation by Purified Polypeptides," Nature, 336:668 (1998).

Thomson, J., et al., "Neural Differentiation of Rhesus Embyronic Stem Cells," APMIS, 106:149 (1998).

Vassilieva, S., et al., "Establishment of SSEA–1– and Oct–4–Expressing Rat Embryonic Stem–like Cell Lines and Effects of Cytokines of the IL–6 Family on Clonal Growth," Exper. Cell Research, 258:361 (2000).

Xiong, J., et al., "Large–Scall Screening for Developmental Genes in Embryonic Stem Cells and Embryoid Bodies Using Retroviral Entrapment Vectors," Dev. Dynamics, 212:181 (1998).

Zandstra, P., et al., "Leukenia Inhibitory Factor (LIF) Concentration Modulates Embryonic Stem Cell Self–Renewal and Differentiation Independently of Proliferation," Biotechnol. Bioeng., 69:607 (2000).

Nichols, J., et al., "Establishment of Germ–line–competent Embryonic Stem (ES) Cells Using Differentiation Inhibiting Activity", Development, 110:1341–1348 (1990).

Nichols, J., et al., "Derivation of Germline Competent Embryonic Stem Cells with a Combination of Interleukin–6 and Soluble Interleukin–6 Receptor", Experimental Cell Res., 215:237–239 (1994).

Baribault, H., et al., "Embryonic Stem Cell Culture and Gene Targeting in Transgenic Mice", Mol. Biol. Med. 6:481–492 (1989).

Becton Dickinson, "Product Specification Sheet: Matrigel Basement Membrane Matrix, Phenol–Red Free".

Berger, C., et al., "Self Renewal of Embryonic Stem Cells in the Absence of Feeder Cells and Exogenous Leukaemia Inhibitory Factor", Growth Factors, 14:145–159 (1997).

Bodnar, A., et al., "Extension of Life–Span by Introduction of Telomerase into Normal Human Cells", Science, 279:349–352 (1998).

Bongso, A., et al., "Improved Quality of Human Embryos When Co–Cultured with Human Ampullary Cells", Hum Reprod., 4:706–713 (1989).

Bradley, A., et al., "Modifying the Mouse: Design and Desire", Biotechnology, 10:534–539 (1992).

Carnici, P., et al., "High–Efficiency Full–Length cDNA Cloning", Methods Enzymol., 303:19–44(1999).

Clontech Laboratories, SMART cDNA Library Construction Kit, Catalog #K1051–1.

Corrick, C., et al., "Construction of a Mouse Blastocyst cDNA Library by PCR Amplification From Total RNA", Molecular Reproduction and Development, 43:7–16 (1996).

Deleersnijder, W., et al., "Isolation of markers for chondro–osteogenic differentiation using cDNA library subtraction. Molecular cloning and characterization of a gene belonging to a novel multigene family of integral membrane proteins", J Biol Chem, 271(32):19475–82 (1996).

Evans, M., et al., "Establishment in Culture of Pluripotential Cell from Mouse Embyros", Nature, 292:154–156 (1981).

Gardner, D., et al., "Culture and Transfer of Human Blostocysts Increases Implantation Rates and Reduces the Need for Multiple Embyro Transfers", Fertil. Steril, 69:84–88 (1998).

Gendall, A., et al., "Isolation and Characterization of a Leukemia Inhibitory Factor–Independent Embyronic Stem Cell Line", Int. J. Biochem Cell Biol., 29(5):829–840 (1997).

Gendron, R., et al., "Induction of Embyronic Vasculogenesis by bFGF and LIF in Vitro and in Vivo", Developmental Biology, 177:332–346 (1996).

GibcoBrl Life Technologies Catalogue and Ref. Guide, pp. 1–2 through 1–4, 1–94 and 1–95 (1993).

Itoh, M., et al., "Automated Filtration–Based High–Throughput Plasmid Preparation System", Genome Res., 9:463–470 (1999).

Itskovitz–Eldor, J., et al., "Differentiation of Human Embyronic Stem Cells into Embyroid Bodies Comprising the Three Embyronic Germ Layers", Mol. Med., 6(2):88–95 (2000).

Keller, G., "In Vitro Differentiation of Embyronic Stem Cells", Cell Biology, 7:862–869 (1995).

Kelly, DL., et al., "DNA Microarray Analyses of Genes Regulated During the Differentiation of Embyronic Stem Cells", Mol. Reprod. Dev., 56(2):113–23 (2000).

Ko, M., et al., "Large–scale cDNA analysis Reveals Phased Gene Expression Patterns During Preimplantation Mouse Development", Development, 127:1737–49 )2000).

Koshimizu, U., et al., "Functional Requirement of gp130–mediated Signaling for Growth and Survival of Mouse Primordial Germ Cells In Vitro and Derivation of Embryonic Germ (EG) Cells", Development, 122:1235–1242 (1996).

Koshimizu, U., et al., "Rapid Communication Retinoic Acid Is a Potent Growth Activator of Mouse Primordial Germ Cells in Vitro", Developmental Biology, 168:683–685 (1995).

Life Technologies, Inc., "SuperScript II; Rnase H Reverse Transcriptase",Product Brochure; pp. 1–4.

Matsui, Y., et al., "Derivation of Pluripotential Embryonic Stem Cells from Murine Primordial Germ Cells in Culture", Cell, 70:841–847 (1992).

Nichols, J., et al., "Establishment of Germ–line–Competent Embryonic Stem (ES) Cells Using Differentiation Inhibiting Activity", Development, 110:1341–1348 (1990).

Nichols, J., et al., "Derivation of Germline Competent Embyronic Stem Cells with a Combination of Interleukin–6 and Soluble Interleukin–6 Receptor", Experimental Cell Research, 215:237–239 (1994).

O'Shea, K., "Embyronic Stem Cell Models of Development", New Anat., 257:32–41 (1999).

Pease, S., et al., "Isolation of Embryonic Stem (ES) Cells in Media Supplemented with Recombinant Leukemia Inhibitory Factor (LIF)", Developmental Biology, 141:344–352 (1990).

Pedersen, R., "Studies of In Vitro Differentiation with Embryonic Stem Cells", Reprod. Fertil. Dev., 6:543–52 (1994).

Pedersen, R., "Embryonic Stem Cell for Medicine", Scientif. Am., 280(4):68–73 (1999).

Rathjen, J., et al., "Formation of a Primitive Ectoderm Like Cell Population, EPL Cells, from ES Cells in Response to Biologically Derived Factors", J. of Cell Sci., 112:601–612 (1999).

Reubinoff, B., et al., "Embryonic Stem Cell Lines From Human Blastocysts: Somatic Differentiation In Vitro", Nat. Biotechnology, 18:399–404 (2000).

Robertson, E., "Derivation and Maintenance of Embyronic Stem Cell Cultures", Methods in Mol. Bio., 75:173–184 (1997).

Rose, T., et al., "Oncostatin M (OSM) Inhibits the Differentiation of Pluripotent Embyronic Stem Cells In Vitro", Cytokine, 6(1):48–54 (1994).

Shamblott, M., et al., "Derivation of Pluripotent Stem Cells from Cultured Human Primordial Germ Cells", Proc. Natl. Acad. Sci. USA, 95:13726–13731 (1998).

Smith, A., et al., "Inhibition of Pluripotential Embryonic Stem Cell Differentiation by Purified Polypeptides", Nature, 336:668–690 (1998).

Sigma, Product Information for Laminins for Cell Culture.

Takahashi, N., et al., "Toward a Whole cDNA Catalog: Construction of an Equalized cDNA library from Mouse Embyros", Genomics, 23(1):202–10 (1994).

Thomson, J., et al., "Embryonic Stem Cell Lines Derived from Human Blastocyts", Science, 282:145–47(1998).

Thomson, J., et al., "Isolation of a Primate Embryonic Stem Cell Line", Proc. Natl. Acad. Sci. USA, 92:7844–7848 (1995).

Thomson, J., et al., "Primate Embryonic Stem Cells", Current Topics in Developmental Biology, 38:133–165 (1998).

Worrall, D., et al., "A Carrot Leucine–Rich–Repeat Protein That Inhibits Ice Recrystallization", Science, 282:115–117 (1998).

Wenk, J., et al., "Glycolipids of Germ Cell Tumors: Extended Globo–Series Glycolipids are a Hallmark of Human Embyronal Carcinoma Cells", Int. J. Cancer, 58:108–115 (1994).

Williams, R., et al., "Myeloid Leukaemia Inhibitory Factor Maintains the Developmental Potential of Embyronic Stem Cells", Nature, 336:684–687 (1988).

Woltjen, K., et al., "Retro–recombination Screening of a Mouse Embyronic Stem Cell Genomic Library", Nucleic Acids Research, 28(9):e41 (2000).

* cited by examiner

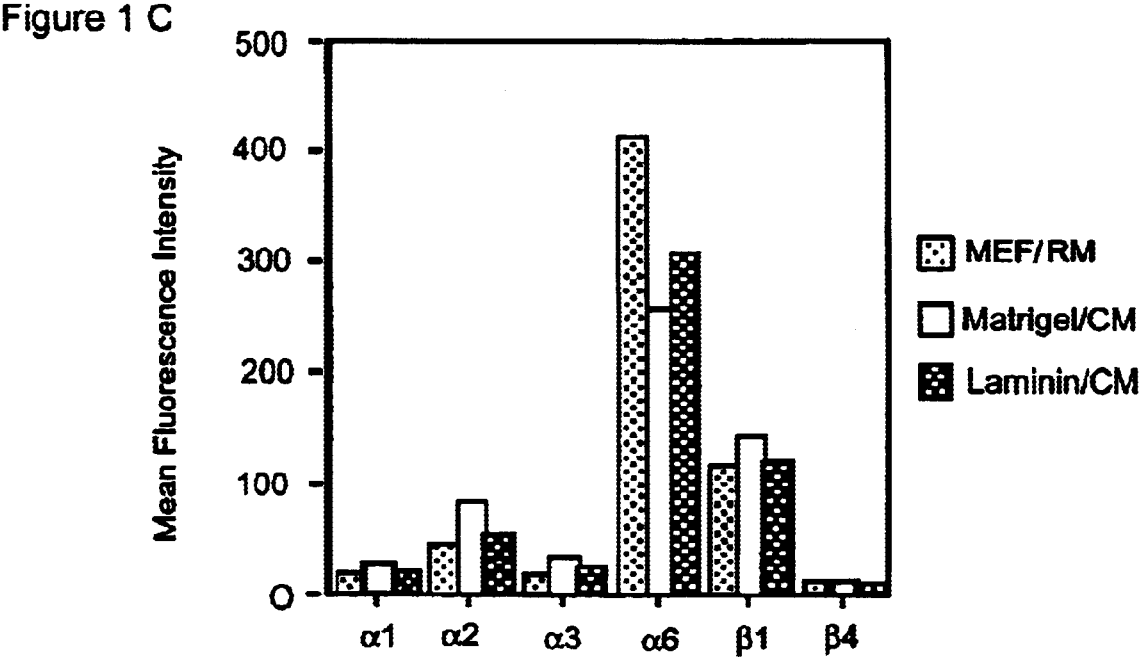

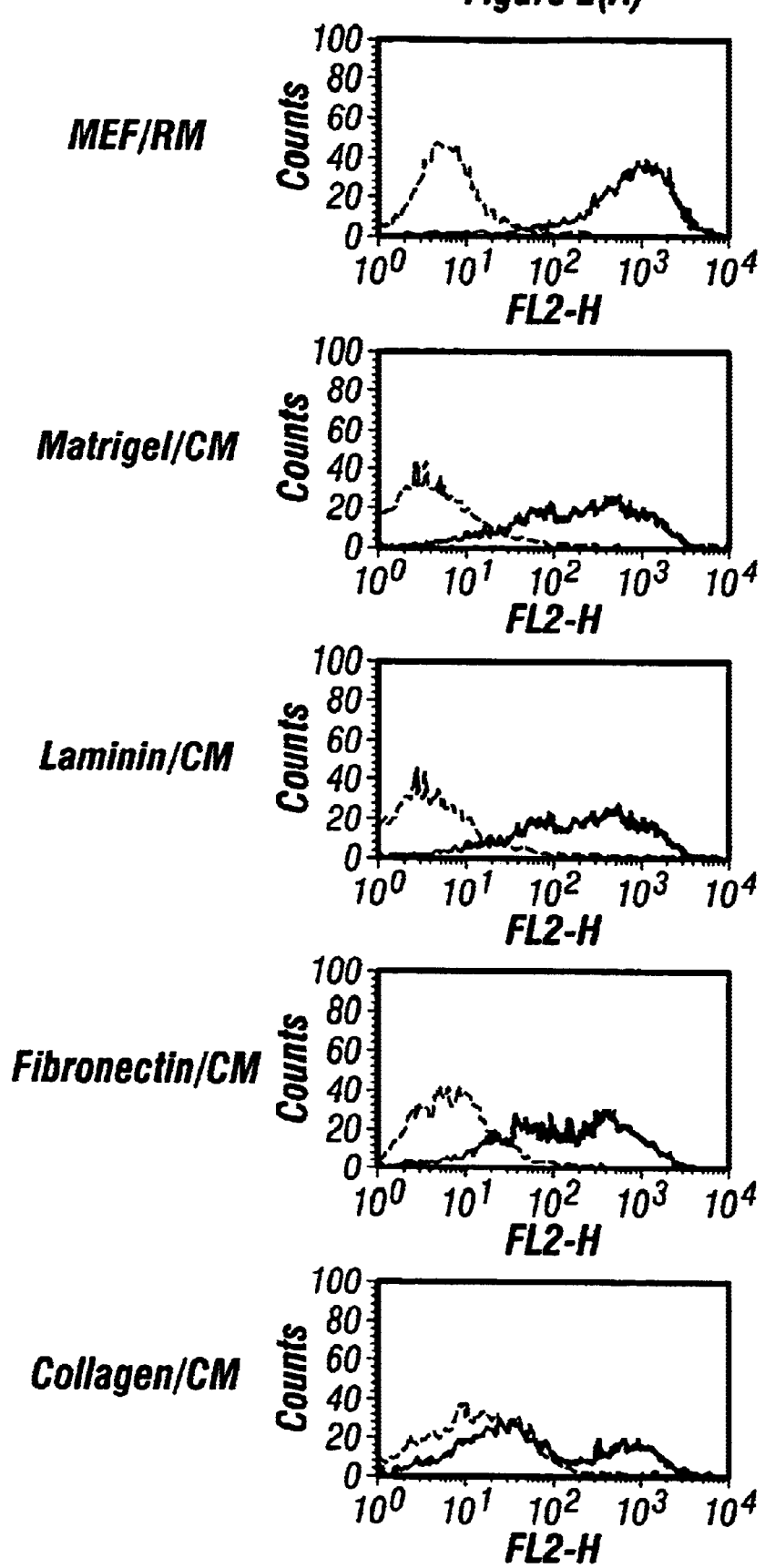

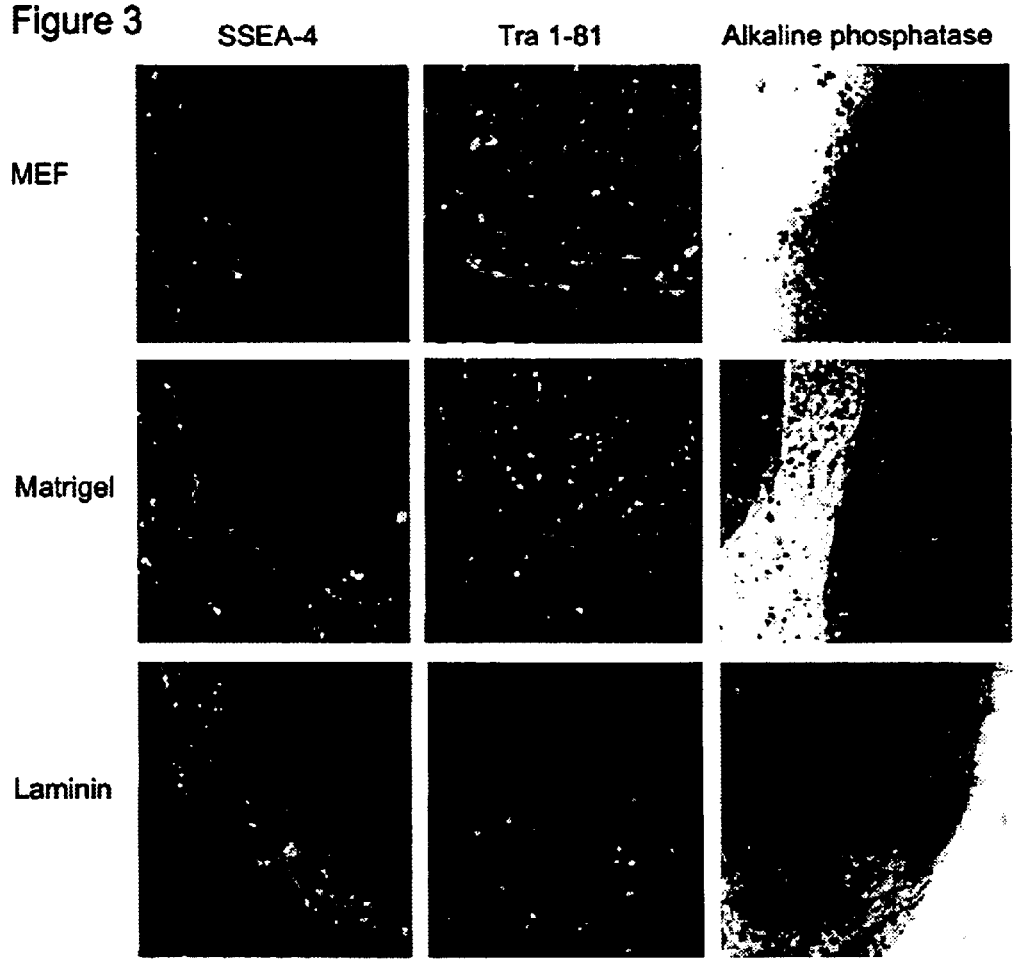

Figure 4 B
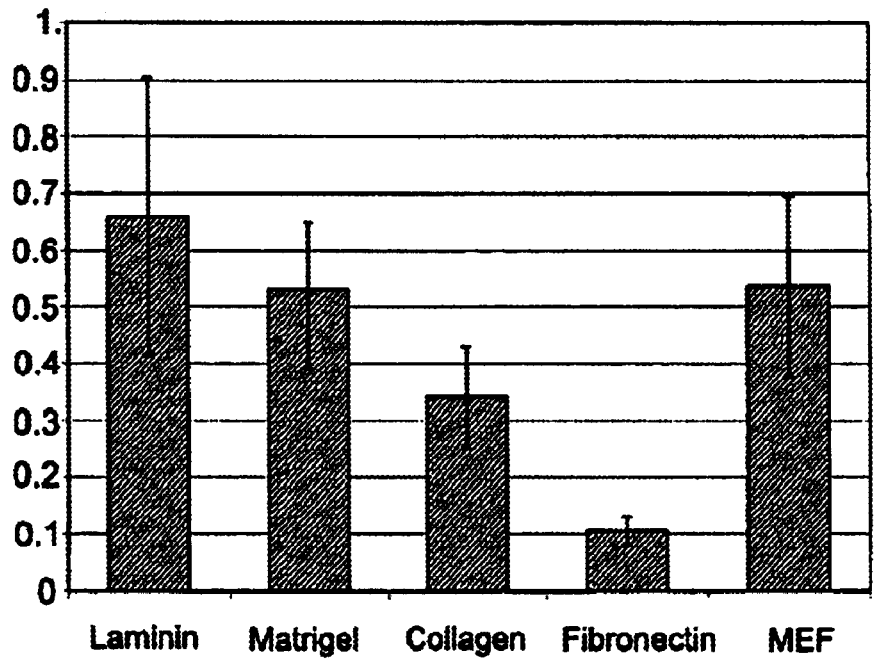
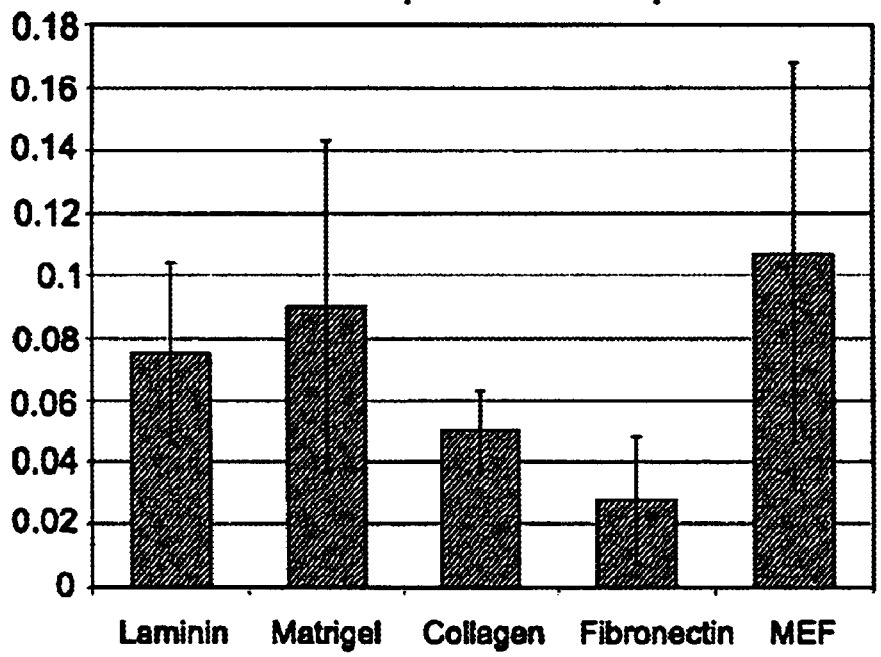

CDNA LIBRARIES REFLECTING GENE EXPRESSION DURING GROWTH AND DIFFERENTIATION OF HUMAN PLURIPOTENT STEM CELLS

REFERENCE TO RELATED APPLICATIONS

This application claims priority to the following pending U.S. provisional patent applications: U.S. Ser. No. 60/175,581, filed Jan. 11, 2000; U.S. Ser. No. 60/213,740, filed Jun. 22, 2000; U.S. Ser. No. 60/213,739, filed Jun. 22, 2000; U.S. Ser. No. 60/216,387, filed Jul. 7, 2000; and U.S. Ser. No. 60/220,064, filed Jul. 21, 2000. The priority applications are hereby incorporated herein by reference in their entirety.

TECHNICAL FIELD

This invention relates generally to the field of cell biology of embryonic cells. More specifically, it relates to the propagation of human pluripotent stem cells, culture conditions that facilitate propagation, and the use of such cultures for producing cDNA libraries.

BACKGROUND

Recent discoveries have raised expectations that stem cells may be a source of replacement cells and tissue for cells and tissues that are damaged in the course of disease, infection, or as a result of congenital abnormalities. Various types of putative stem cells differentiate when they divide, maturing into cells that can carry out the unique functions of particular tissues, such as the heart, the liver, or the brain. A particularly important discovery has been the development of pluripotent stem cells, which are thought to have the potential to differentiate into almost any cell type.

Early work on pluripotent stem cells was done in mice (reviewed in Robertson, Meth. Cell Biol. 75:173, 1997; and Pedersen, Reprod. Fertil. Dev. 6:543, 1994). Mouse stem cells can be isolated both from early embryonic cells and germinal tissue. Desirable characteristics of pluripotent stem cells are that they be capable of indefinite proliferation in vitro in an undifferentiated state, retain a normal karyotype, and retain the potential to differentiate to derivatives of all three embryonic germ layers (endoderm, mesoderm, and ectoderm).

Expression libraries produced from mouse embryonic stem cells have been reported and the resulting sequences deposited in public databases (e.g., GenBank entries from the Washington University-Howard Hughes Medical Institute Mouse EST Project; RIKEN Institute Mouse ESTs). Typically, these libraries are constructed by first isolating mRNA from in vitro cultured mouse ES strains, then converting the mRNA to double-strand cDNA. Plasmid clones from such libraries are processed and DNA sequence is obtained from one or both ends of the cDNAs.

U.S. Pat. No. 5,789,158 (Knowles) reported production of cDNA libraries made from mRNA taken from unfertilized eggs, embryos, and 8-cell blastocysts. Subtraction libraries were reported from 2-cell and 8-cell stage embryos. Insert size of the cDNA in positive clones ranged from 500 to 900 base pairs. Adjaye et al. (Genomics 46:337, 1997) reported cDNA libraries formed from unfertilized oocytes, and embryos up to the blastocyst stage. The authors found that a high proportion of detected sequences were not found in the GenBank dbEST databases.

Nishiguichi et al. (J. Biochem. 119:749, 1996) used ESTs to identify genes expressed in mouse embryonal carcinoma F9 cells. Of 1026 randomly selected cDNA clones, 78% matched known genes, of which 53% were related to transcription and translation, and 19% were related to energy metabolism. Approximately 7% of the ESTs corresponding to low-abundance mRNAs were reported as related to retinoic acid-regulated genes, or mammalian development or differentiation related genes.

Sasaki et al (Genomics 49:167, 1998) reported gene expression in mouse blastocyst by single-pass EST sequencing of 3995 clones. Analysis of the cDNAs revealed that the library contained a variety of genes that did not match with homologs in the human EST database. The authors concluded that many early stage developmental genes remain to be identified.

Phillips et al. (Science 288:1635, 2000) analyzed the genetic program of hematopoietic stem cells. Subtracted cDNA libraries from purified murine fetal liver stem cells were analyzed with bioinformatic and array hybridization strategies. Several thousand previously undescribed gene products were determined, with properties suggestive of regulatory functions. Collected data on the molecular phenotype of the murine hematopoietic stem cell is available at the Princeton stem cell website.

Challenges in the Characterization and use of Human Pluripotent Stem Cells

The development of preparations of human pluripotent stem cells has involved overcoming a number of technical difficulties, and is considerably less advanced than work with mouse cells.

Thomson et al. (U.S. Pat. No. 5,843,780; Proc. Natl. Acad. Sci. USA 92:7844, 1995) were the first to successfully isolate and propagate pluripotent stem cells from primates. They subsequently derived human embryonic stem (hES) cell lines from human blastocysts (Science 282:114, 1998). Gearhart and coworkers derived human embryonic germ (hEG) cell lines from fetal gonadal tissue (Shamblott et al., Proc. Natl. Acad. Sci. USA 95:13726, 1998; and U.S. Pat. No. 6,090,622).

Both hES and hEG cells have the long-sought characteristics of pluripotent stem cells: they are capable of long-term proliferation in vitro without differentiating, they have a normal karyotype, and they remain capable of producing a number of different cell types. Because of this, they hold considerable promise for use in human therapy, acting as a reservoir for regeneration of almost any tissue compromised by genetic abnormality, trauma, or a disease condition.

A significant challenge to the use of pluripotent stem cells for therapy is that they are traditionally cultured on a layer of feeder cells to prevent differentiation (U.S. Pat. No. 5,843,780; U.S. Pat. No. 6,090,622). Without feeder fibroblasts in the culture environment, hPS cells soon die, or differentiate into a heterogeneous population of committed cells. Leukemia inhibitory factor (LIF) inhibits differentiation of mouse PS cells, but it does not replace the role of feeder cells in preventing differentiation of human PS cells. Unfortunately, using feeder cells increases production costs, impairs scale-up, and produces mixed cell populations that require the pluripotent stem cells be separated from feeder cell components.

Another challenge is to control differentiation of stem cells into the particular type of tissue required for treatment of each patient. It is a hypothesis of this invention that better understanding of the differentiation process will be obtained by observing gene expression during growth and differentiation of pluripotent stem cells.

International Patent Publication WO 99/20741 (Geron Corp.) is entitled Methods and Materials for the Growth of Primate-Derived Primordial Stem Cells. In one embodiment, a cell culture medium is provided for growing primate-derived primordial stem cells in a substantially undifferentiated state, having a low osmotic pressure and low endotoxin levels. The basic medium is combined with a nutrient serum effective to support the growth of primate-derived primordial stem cells and a substrate of feeder cells or an extracellular matrix component derived from feeder cells. The medium further includes non-essential amino acids, an anti-oxidant, and growth factors which are either nucleosides or a pyruvate salt.

Sequence-based studies of early human development have focused on libraries produced from fetal organs and tissues for example, fetal libraries from the I.M.A.G.E. consortium. International Patent Publication WO 98/00540 (Incyte) reports partial sequences of stem cell antigens, isolated from cDNA libraries derived from THP-1 cells and bladder tumors.

As far as we know, successful production and characterization of expression libraries from human pluripotent stem cells or their derivatives has not previously been reported.

SUMMARY OF THE INVENTION

Described in this disclosure is a system for obtaining expression libraries from primate pluripotent stem (pPS) cells. pPS cells can be maintained in vitro without requiring a layer of feeder cells to inhibit differentiation. The role of the feeder cells is replaced by culture conditions that promote hPS cell growth without differentiation, exemplified by an extracellular matrix and conditioned medium. cDNA libraries from such cultures are substantially devoid of transcripts of feeder cell origin, relatively uncontaminated by transcripts from differentiated cells, and can have a high proportion of full-length transcripts. Subtraction libraries can also be produced that are enriched for transcripts modulated during differentiation.

Some embodiments of the invention are methods for obtaining an mRNA preparation or a cDNA library from primate pluripotent stem (pPS) cells before or after differentiation, comprising providing a culture of undifferentiated pPS cells essentially free of feeder cells, optionally permitting the pPS cells to differentiate, and isolating mRNA from the undifferentiated or differentiated cells. cDNA libraries are formed by recombining cDNA copies of the mRNA into a cloning vector. Optionally, the cloning vector is also an expression vector, in which cDNA is operatively linked to a transcriptional regulatory control element, such as the PGK promoter that promotes transcription of the cDNA in undifferentiated pPS cells.

Included are methods of obtaining mRNA preparations and expression libraries that represent transcripts found in undifferentiated pPS cells, and cells differentiated into committed precursors and other cell types. Also included are methods of obtaining subtraction libraries, enriched for transcripts differently expressed in two cell types, which involves incubating together preparations of mRNA (or cDNA copies thereof) obtained from two cell populations under conditions that permit polynucleotides present in both preparations to cross-hybridize; and then recombining polynucleotides that have not cross-hybridized into a cloning vector. The cell populations may be undifferentiated and differentiated pPS cells, two types of differentiated pPS cells, or cells that have been exposed to a compound or environment that influences expression patterns (in comparison with control cells).

In certain embodiments, these methods involve pPS cells essentially free of feeder cells maintained in a culture environment comprising an extracellular matrix, and a medium pre-conditioned using feeder cells. Suitable feeder cells include euploid human cell lines that can be maintained in culture for at least 60 days. Various types of pPS cells can be used, including human embryonic stem (hES) cells.

Other embodiments of the invention are expression libraries with certain characteristics described in this disclosure. Exemplary is a cDNA library containing at least 100, 1,000, or 10,000 genes expressed at the mRNA level in undifferentiated pPS cells or their differentiated progeny, essentially free of cDNA of other vertebrates. Also included are subtraction libraries in which at least 20 to 50% of the cDNA is from genes that are modulated during differentiation of pPS cells. As much as 30% of cDNA inserts in the library comprise the entire encoding region of the corresponding mRNA.

Other embodiments of the invention are expression libraries made according to the methods described or exemplified in this disclosure.

Further embodiments of the invention are methods for producing a polynucleotide containing a sequence of an mRNA expressed in undifferentiated or differentiated pPS cells, or a polypeptide expressed in undifferentiated or differentiated pPS cells, or an antibody specific for such a polypeptide. The methods involve determining the sequence from mRNA or cDNA of this invention, and using the sequence data to manufacture the polynucleotide, polypeptide, or antibody. The corresponding gene may be expressed constitutively, or it may be upregulated or downregulated when pPS cells differentiate, or are exposed to particular environmental agents or metabolic changes.

These and other aspects of the invention will be apparent from the description that follows.

BRIEF DESCRIPTION OF THE FIGURES

FIG. 3 is a half-tone reproduction of micrographs showing marker expression detected by immunohistochemistry for cells grown with primary feeder cells (mEF) or on the extracellular matrices Matrigel® or laminin in conditioned medium. hES cells grown in feeder-free culture have phenotypic markers similar to those of hES grown on mouse fibroblast feeder cells.

DETAILED DESCRIPTION

Figure 1:
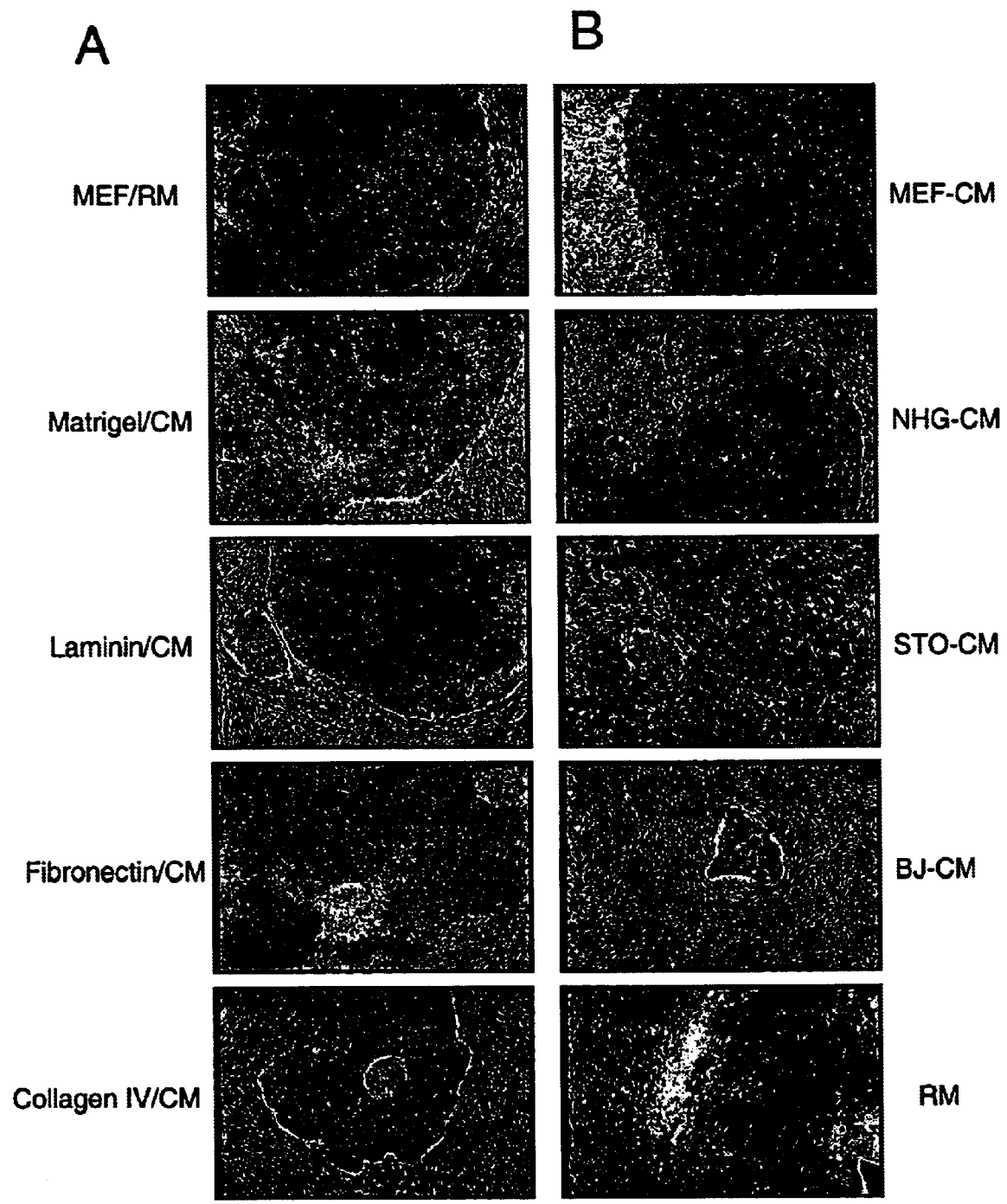
FIG. 1 is a half-tone reproduction of photomicrographs showing the morphology of hES cells in feeder-free culture. Panel A (Left Side) shows morphology of hES cells cultured on feeder cells in regular culture medium (mEF/RM), or on Matrigel®, laminin, fibronectin, or collagen IV in mEF conditioned medium. Panel B (Right Side) shows morphology of hES cells maintained on Matrigel® in medium conditioned by mEF, NHG 190, STO and BJ cells, compared with unconditioned regular medium (RM). The cells in RPE conditioned medium differentiated within the first week of culture. The cells in the other conditioned media all had hES colonies with appropriate ES-morphology. Panel C is a bar graph showing integrin expression measured in hES cells maintained on feeders in regular medium (mEF/RM) or on Matrigel®; or on laminin in mEF conditioned medium. Integrin components α6 and β1 may play a role in adherence of hES cells to extracellular matrix.

This disclosure provides a system for obtaining expression libraries from primate pluripotent stem (pPS) cells. pPS cells can be maintained in vitro without requiring a layer of feeder cells to inhibit differentiation.

It has been found that the role of the feeder cells can be replaced by a combination of one or more features in the culture environment that support proliferation of the cells without differentiation. One such feature is a suitable substrate on the culture surface, such as extracellular matrix exemplified by Matrigel® and laminin. Another feature is the use of culture media containing factors that in some way effectively inhibit differentiation, exemplified by conditioned media. Cells for conditioning media to support pPS cells include primary embryonic fibroblasts, telomerized fibroblasts, and fibroblast-like cells differentiated and selected from cultured pPS cells.

In an exemplary preparation, undifferentiated hES colonies were harvested from hES cultures on feeders, and then seeded onto a Matrigel® substrate in conditioned medium at approximately 15 colonies to each 9.6 $cm^2$ well. The day after seeding, undifferentiated hES cells were visible as small colonies of about 100–2,000 cells, and there were single cells in-between the colonies that appeared to be differentiating or dying. As the hES cells proliferated, colonies became large and compact, representing the majority of surface area of the culture dish. Near confluence, most of the cells had morphological characteristics of undifferentiated cells, and differentiated cells in between the colonies represented less than 10% of the cells in the culture.

Doubling rate was of the order of 20–40 hours, which is comparable to hES grown on feeder cells. Medium was changed daily, and the cells were split and passaged every 6 or 7 days. Nineteen days after initial seeding, the cells were tested for cell surface phenotype by immunofluorescence. Over 90% of the cells stained positively for SSEA-4 and Tra-1-60; over 80% stained positively for Tra-1-81, but less than 15% stained positively for SSEA-1. This indicates that at least about 80% of the cells in the preparation had the phenotype expected for undifferentiated hES cells.

Culturing pPS cells in a feeder-free environment provides a number of important advantages for the preparation of gene expression libraries:

The proportion of undifferentiated pPS cells in the culture tends to be higher, which improves the yield of mRNA per $cm^2$. This facilitates production of the cDNA libraries.

The library is not contaminated by transcripts from feeder cells (either cDNA of a different species, or cDNA from a separate human cell line with a different expression pattern than undifferentiated pPS cells).

High-yield mRNA from pPS uncontaminated with feeder cell mRNA permits construction of libraries enriched for full-length encoding regions of rare transcripts that may be unique to pPS cells during propagation or differentiation.

Differentiation of PS cells is facilitated in feeder-free culture. Embryoid bodies can be formed that are smaller in diameter and less likely to contain necrotic interiors. pPS cells can also be differentiated directly on the original culture plate by replacing medium that inhibits differentiation with medium that promotes differentiation along one or a plurality of committed cell lineages.

Since subtraction is not needed to remove transcripts from feeder cells, first-level subtraction can be performed to obtain representative libraries enriched for transcripts modulated during development.

Certain expression libraries of this invention are optimized for expression of the cDNA in pluripotent stem cells. Transcription control mechanisms in embryonic cells suppress the activity of promoters often used for recombinant gene expression. It has been discovered that promoters for house-keeping genes active in pPS cells can be effective. Using an empirical selection strategy, the promoter for phosphoglycerate kinase (PGK) has been determined as effective for expression of cDNA in pPS cells.

Libraries prepared according to this invention are useful for isolating and characterizing genes expressed in undifferentiated pPS cells and their differentiated progeny. The information can be used for a number of important purposes, including the testing and manipulation of factors that play a role in the differentiation process. DNA, protein, and antibodies can be prepared from the expressed transcripts, and used for characterizing or manipulating pPS cell growth and differentiation.

Additional features of the invention are described in the sections that follow.

Definitions

Prototype "primate Pluripotent Stem cells" (pPS cells) are pluripotent cells derived from pre-embryonic, embryonic, or fetal tissue at any time after fertilization, and have the characteristic of being capable under the right conditions of producing progeny of several different cell types. pPS cells are capable of producing progeny that are derivatives of all of the three germinal layers: endoderm, mesoderm, and ectoderm, according to a standard art-accepted test, such as the ability to form a teratoma in a suitable host.

Included in the definition of pPS cells are embryonic cells of various types, exemplified by human embryonic stem (hES) cells, as described by Thomson et al. (Science 282:1145, 1998); embryonic stem cells from other primates, such as Rhesus or marmoset stem cells described by Thomson et al. (Proc. Natl. Acad. Sci. USA 92:7844, 1995); and human embryonic germ (hEG) cells, described in Shamblott et al. (Proc. Natl. Acad. Sci. USA 95:13726, 1998). Other types of pluripotent cells are also included in the term. Any cells of primate origin that are capable of producing progeny that are derivatives of all three germinal layers are included, regardless of whether they were derived from embryonic tissue, fetal tissue, or other sources. For many embodiments of the invention, it is beneficial to use pPS cells that are karyotypically normal and not derived from a malignant source.

pPS cell cultures are described as "undifferentiated" or "substantially undifferentiated" when a substantial proportion of stem cells and their derivatives in the population display morphological characteristics of undifferentiated cells, clearly distinguishing them from differentiated cells of embryo or adult origin. Undifferentiated pPS cells are easily recognized by those skilled in the art, and typically appear in the two dimensions of a microscopic view with high nuclear/cytoplasmic ratios and prominent nucleoli It is understood that colonies of undifferentiated cells within the population will often be surrounded by neighboring cells that are differentiated. Nevertheless, the undifferentiated colonies persist when the population is cultured or passaged under appropriate conditions, and individual undifferentiated cells constitute a substantial proportion of the cell population. Cultures that are substantially undifferentiated contain at least 20% undifferentiated pPS cells, and may contain at least 40%, 60%, or 80% in order of increasing preference (in terms percentage of cells with the same genotype that are undifferentiated). Using the methods described in this disclosure, it is sometimes possible to develop or passage cultures that contain a relatively low proportion of differentiated pPS cells (even as low as 5 or 10%) into cultures that are substantially undifferentiated.

Whenever a culture or cell population is referred to in this disclosure as proliferating "without differentiation", what is meant is that after proliferation, the composition is substantially undifferentiated according to the preceding definition. Populations that proliferate through at least 4 passages (~20 doublings) without differentiation will contain substantially the same proportion of undifferentiated cells (or possibly a higher proportion of undifferentiated cells) when evaluated at the same degree of confluence as the originating culture.

"Feeder cells" or "feeders" are terms used to describe cells of one type that are co-cultured with cells of another type, to provide an environment in which the cells of the second type can grow. The feeder cells are optionally from a different species as the cells they are supporting. For example, certain types of pPS cells can be supported by primary cultures of mouse embryonic fibroblasts, immortalized mouse embryonic fibroblasts, or human fibroblast-like cells differentiated from hES cells, as described later in this disclosure. In coculture with pPS cells, feeder cells are typically inactivated by irradiation or treatment with an anti-mitotic agent such as mitomycin c, to prevent them from outgrowing the cells they are supporting. For use in producing conditioned medium, inactivation of the cells may be optional, and depends in part on mechanical aspects of medium production.

pPS cell populations are said to be "essentially free" of feeder cells if the cells have been grown through at least one round after splitting in which fresh feeder cells are not added to support the growth of the pPS. It is recognized that if a previous culture containing feeder cells is used as a source of pPS for the culture to which fresh feeders are not added, there will be some feeder cells that survive the passage. For example, hES cells are often cultured in a 9.6 $cm^2$ well on a surface of ~375,000 primary irradiated embryonic fibroblasts near confluence. By the end of the culture, perhaps 150,000 feeder cells are still viable, and will be split and passaged along with hES that have proliferated to a number of ~1 to 1.5 million. After a 1:6 split, the hES cells generally resume proliferation, but the fibroblasts will not grow and only a small proportion will be viable by the end of ~6 days of culture. This culture is essentially free of feeder cells, with compositions containing less than about 5% feeder cells. Compositions containing less than 1%, 0.2%, 0.05%, or 0.01% feeder cells (expressed as % of total cells in the culture) are increasingly more preferred.

Whenever a culture or cell population is referred to in this disclosure as "feeder-free", what is meant is that the composition is essentially free of feeder cells according to the preceding definition, subject only to further constraints if explicitly required.

A "growth environment" is an environment in which cells of interest will proliferate in vitro. Features of the environment include the medium in which the cells are cultured, the temperature, the partial pressure of $O_2$ and $CO_2$, and a supporting structure (such as a substrate on a solid surface) if present.

A "nutrient medium" is a medium for culturing cells containing nutrients that promote proliferation. The nutrient medium may contain any of the following in an appropriate combination: isotonic saline, buffer, amino acids, antibiotics, serum or serum replacement, and exogenously added factors. A "conditioned medium" is prepared by culturing a first population of cells in a medium, and then harvesting the medium. The conditioned medium (along with anything secreted into the medium by the cells) may then be used to support the growth of a second population of cells.

"Restricted developmental lineage cells" are cells derived from embryonic tissue, typically by differentiation or partial differentiation of pPS cells. These cells are capable of proliferating and differentiating into several different cell types, but the range of their repertory is restricted. Examples are hematopoietic cells, which are pluripotent for blood cell types, and hepatocyte progenitors, which are pluripotent for sinusoidal endothelial cells, hepatocytes, and potentially other liver cells. Another example is neural restricted cells, which can generate glial cell precursors that progress to oligodendrocytes and astrocytes, and neuronal precursors that progress to neurons.

The term "polynucleotide" refers to a polymeric form of nucleotides of any length. Included are genes and gene fragments, mRNA, tRNA, rRNA, ribozymes, cDNA, recombinant polynucleotides, branched polynucleotides, plasmids, vectors, isolated DNA and RNA, nucleic acid probes, and primers. As used in this disclosure, the term polynucleotides refers interchangeably to double- and single-stranded molecules. Unless otherwise specified or required, any embodiment of the invention that is a polynucleotide encompasses both a double-stranded form, and each of the two complementary single-stranded forms known or predicted to make up the double-stranded form. When comparison is made between polynucleotides for degree of identity, it is implicitly understood that complementary strands are easily generated, and the sense or antisense strand is selected or predicted that maximizes the degree of identity between the polynucleotides being compared. Percentage of sequence identity is calculated by first aligning the polynucleotide being examined with the reference counterpart, and then counting the number of residues shared between the sequences being compared as a percentage of the region under examination, without penalty for the presence of obvious insertions or deletions.

A "control element" or "control sequence" is a nucleotide sequence involved in an interaction of molecules that contributes to the functional regulation of a polynucleotide, such as replication, duplication, transcription, splicing, translation, or degradation of the polynucleotide. Transcriptional control elements include promoters and enhancers.

Genetic elements are "operatively linked" if they are in a structural relationship permitting them to operate in a manner according to their expected function. For instance, a promoter is operatively linked to a coding region if the promoter helps initiate transcription of the coding sequence. There may be intervening sequence between the promoter and coding region so long as this functional relationship is maintained.

A "cloning vector" is a polynucleotide vehicle (such as a plasmid, bacterophage, or plant or animal virus) that permits replication of a sequence inserted into the vehicle in a host cell. In the case of a cDNA library, the replicated vectors contain heterogeneous polynucleotide inserts copied from a heterogeneous mRNA preparation transcribed from a plurality of genes. If the inserts are operatively linked to a transcriptional regulatory control element that permit expression of the insert at the protein or mRNA level in a host cell, the vehicle can also referred to as an "expression vector".

The terms "polypeptide", "peptide" and "protein" are used interchangeably in this disclosure to refer to polymers of amino acids of any length. The polymer may comprise modified amino acids, it may be linear or branched, and it may be interrupted by non-amino acids. Percentage of sequence identity is calculated for polypeptides by first aligning the polypeptide being examined with the reference counterpart or prototype, and then counting the number of residues shared between the sequences being compared as a percentage of the region under examination, without penalty for the presence of insertions or deletions. Where substitutions are made, conservative substitutions (in which one amino acid is substituted by another with similar charge, size, hydrophobicity, or aromaticity) are typically better tolerated. Desirable sequences preserves the function of the prototype: for example, the enzymatic activity, the binding of specific substrates, and the binding of specific antibody as detectable in a standard competition inhibition immunoassay.

A cell is said to be "genetically altered", "transfected", or "genetically transformed" when a polynucleotide has been transferred into the cell by any suitable means of artificial manipulation, or where the cell is a progeny of the originally altered cell that has inherited the polynucleotide. The polynucleotide will often comprise a transcribable sequence encoding a protein of interest, which enables the cell to express the protein at an elevated level. Also included are genetic alterations by any means that result in functionally altering or abolishing the action of an endogenous gene. The genetic alteration is said to be "inheritable" if progeny of the altered cell have the same alteration.

The term "antibody" as used in this disclosure refers to both polyclonal and monoclonal antibody. The ambit of the term deliberately encompasses not only intact immunoglobulin molecules, but also such fragments and derivatives of immunoglobulin molecules (such as single chain Fv constructs), and fragments and derivatives of immunoglobulin equivalents such as T-cell receptors, as may be prepared by techniques known in the art, and retaining the desired antigen binding specificity.

General Techniques

For further elaboration of general techniques useful in the practice of this invention, the practitioner can refer to standard textbooks and reviews in cell biology, tissue culture, and embryology. Included are *Teratocarcinomas and embryonic stem cells: A practical approach* (E. J. Robertson, ed., IRL Press Ltd. 1987); *Guide to Techniques in Mouse Development* (P. M. Wasserman et al., eds., Academic Press 1993); *Embryonic Stem Cell Differentiation in Vitro* (M. V. Wiles, Meth. Enzymol. 225:900, 1993); *Properties and uses of Embryonic Stem Cells: Prospects for Application to Human Biology and Gene Therapy* (P. D. Rathjen et al., al.,1993). Differentiation of stem cells is reviewed in Robertson, Meth. Cell Biol. 75:173, 1997; and Pedersen, Reprod. Fertil. Dev. 10:31, 1998.

Methods in molecular genetics and genetic engineering are described generally in the current editions of *Molecular Cloning: A Laboratory Manual*, (Sambrook et al.); *Oligonucleotide Synthesis* (M. J. Gait, ed.,); *Animal Cell Culture* (R. I. Freshney, ed.); *Gene Transfer Vectors for Mammalian Cells* (Miller & Calos, eds.); *Current Protocols in Molecular Biology and Short Protocols in Molecular Biology, 3rd Edition* (F. M. Ausubel et al., eds.); and *Recombinant DNA Methodology* (R. Wu ed., Academic Press). Reagents, cloning vectors, and kits for genetic manipulation referred to in this disclosure are available from commercial vendors such as BioRad, Stratagene, Invitrogen, and ClonTech.

For general techniques involved in preparation of mRNA and cDNA libraries and their analysis, those skilled in the art have access to *RNA Methodologies: A Laboratory Guide for Isolation and Characterization* (R. E. Farrell, Academic Press, 1998); *cDNA Library Protocols* (Cowell & Austin, eds., Humana Press); *Functional Genomics* (Hunt & Livesey, eds., 2000); and the *Annual Review of Genomics and Human Genetics* (E Lander, ed., published yearly by Annual Reviews). Techniques can also be inferred from descriptions of other expression libraries, for example: Developmental Embryonic Mouse Libraries (U.S. Pat. No. 5,789,158); Method for Generating a Subtracted cDNA Library (U.S. Pat. No. 5,643,761); Comparative Gene Transcript Analysis (WO 95/20681, Incyte Pharmaceuticals); *A Gene Trap Approach in Mouse Embryonic Stem Cells* (Skarnes et al., Genes Dev. 6:903, 1992); Sasaki et al., Genomics 49:167, 1998; Adjaye et al., Genomics 46:337, 1997; Nishiguchi et al., J. Biochem. 119:749, 1996; and Phillips et al., Science 288:1635, 2000.

General techniques used in raising, purifying and modifying antibodies, and the design and execution of immunoassays including immunohistochemistry, the reader is referred to *Handbook of Experimental Immunology* (Weir & Blackwell, eds.); *Current Protocols in Immunology* (Coligan et al., eds.); and *Methods of Immunological Analysis* (Masseyeff et al., eds., Weinheim: VCH Verlags GmbH).

Media and Feeder Cells

Media for isolating and propagating pPS cells can have any of several different formulas, as long as the cells obtained have the desired characteristics, and can be propagated further. Suitable sources are as follows: Dulbecco's modified Eagles medium (DMEM), Gibco # 11965-092; Knockout Dulbecco's modified Eagles medium (KO DMEM), Gibco # 10829-018; 200 mM L-glutamine, Gibco # 15039-027; non-essential amino acid solution, Gibco 11140-050; β-mercaptoethanol, Sigma # M7522; human recombinant basic fibroblast growth factor (bFGF), Gibco # 13256-029. Exemplary serum-containing ES medium is made with 80% DMEM (typically KO DMEM), 20% defined fetal bovine serum (FBS) not heat inactivated, 1% non-essential amino acids, 1 mM L-glutamine, and 0.1 mM β-mercaptoethanol. The medium is filtered and stored at 4° C. for no longer than 2 weeks. Serum-free ES medium is made with 80% KO DMEM, 20% serum replacement, 1% non-essential amino acids, 1 mM L-glutamine, and 0.1 mM β-mercaptoethanol. Not all serum replacements work; an effective serum replacement is Gibco # 10828-028 (proprietary formula; product obtainable from the manufacturer). The medium is filtered and stored at 4° C. for no longer than 2 weeks. Just before use, human bFGF is added to a final concentration of 4 ng/mL.

pPS cells are typically cultured on a layer of feeder cells which support the pPS cells in various ways, such as the production of soluble factors that promote pPS cell survival or proliferation, or inhibit differentiation. Feeder cells are typically fibroblast type cells, often derived from embryonic or fetal tissue. A frequently used source is mouse embryo. Useful feeder cell lines have been obtained by obtaining embryonic fibroblasts, transfecting them to express telomerase, and then passaging them or freezing them for future use. The cell lines are plated to near confluence, irradiated to prevent proliferation, and used to support pPS cell cultures.

In one illustration, pPS cells are first derived and supported on primary embryonic fibroblasts. Mouse embryonic fibroblasts (mEF) can be obtained from outbred CF1 mice (SASCO) or other suitable strains. The abdomen of a mouse at 13 days of pregnancy is swabbed with 70% ethanol, and the decidua is removed into phosphate buffered saline (PBS). Embryos are harvested; placenta, membranes, and soft tissues are removed; and the carcasses are washed twice in PBS. They are then transferred to fresh 10 cm bacterial dishes containing 2 mL trypsin/EDTA, and finely minced. After incubating 5 min at 37° C., the trypsin is inactivated with 5 mL DMEM containing 10% FBS, and the mixture is transferred to a 15 mL conical tube. Debris is allowed to settle for 2 min, the supernatant is made up to a final volume of 10 mL, and plated onto a 10 cm tissue culture plate or T75 flask. The flask is incubated undisturbed for 24 h, after which the medium is replaced. When flasks are confluent (~2–3 d), they are split 1:2 into new flasks.

Feeder cells are propagated in mEF medium, containing 90% DMEM (Gibco # 11965-092), 10% FBS (Hyclone # 30071-03), and 2 mM glutamine. mEFs are propagated in T150 flasks (Corning # 430825), splitting the cells 1:2 every other day with trypsin, keeping the cells subconfluent. To prepare the feeder cell layer, cells are irradiated at a dose to inhibit proliferation but permit synthesis of important factors that support hES cells (~4000 rads gamma irradiation). Six-well culture plates (such as Falcon # 304) are coated by incubation at 37° C. with 1 mL 0.5% gelatin per well overnight, and plated with 375,000 irradiated mEFs per well. Feeder cell layers are used 5 h to 4 days after plating. The medium is replaced with fresh hES medium just before seeding pPS cells.

Preparation of Human Embryonic Stem (hES) Cells

Human embryonic stem (hES) cells can be prepared as described by Thomson et al. (U.S. Pat. No. 5,843,780; Science 282:1145, 1998; Curr. Top. Dev. Biol. 38:133 ff., 1998; Proc. Natl. Acad. Sci. USA 92:7844, 1995).

Briefly, human blastocysts are obtained from human in vivo preimplantation embryos. Alternatively, in vitro fertilized (IVF) embryos can be used, or one cell human embryos can be expanded to the blastocyst stage (Bongso et al., Hum Reprod 4: 706, 1989). Human embryos are cultured to the blastocyst stage in G1.2 and G2.2 medium (Gardner et al., Fertil. Steril. 69:84, 1998). Blastocysts that develop are selected for ES cell isolation. The zona pellucida is removed from blastocysts by brief exposure to pronase (Sigma). The inner cell masses are isolated by immunosurgery, in which blastocysts are exposed to a 1:50 dilution of rabbit anti-human spleen cell antiserum for 30 minutes, then washed for 5 minutes three times in DMEM, and exposed to a 1:5 dilution of Guinea pig complement (Gibco) for 3 min (see Solter et al., Proc. Natl. Acad. Sci. USA 72:5099, 1975). After two further washes in DMEM, lysed trophectoderm cells are removed from the intact inner cell mass (ICM) by gentle pipetting, and the ICM plated on mEF feeder layers.

After 9 to 15 days, inner cell mass-derived outgrowths are dissociated into clumps either by exposure to calcium and magnesium-free phosphate-buffered saline (PBS) with 1 mM EDTA, by exposure to dispase or trypsin, or by mechanical dissociation with a micropipette; and then replated on mEF in fresh medium. Dissociated cells are replated on mEF feeder layers in fresh ES medium, and observed for colony formation. Colonies demonstrating undifferentiated morphology are individually selected by micropipette, mechanically dissociated into clumps, and replated. ES-like morphology is characterized as compact colonies with apparently high nucleus to cytoplasm ratio and prominent nucleoli. Resulting ES cells are then routinely split every 1–2 weeks by brief trypsinization, exposure to Dulbecco's PBS (without calcium or magnesium and with 2 mM EDTA), exposure to type IV collagenase (~200 U/mL; Gibco) or by selection of individual colonies by micropipette. Clump sizes of about 50 to 100 cells are optimal.

Preparation of Human Embryonic Germ (hEG) Cells

Human Embryonic Germ (hEG) cells can be prepared from primordial germ cells present in human fetal material taken about 8–11 weeks after the last menstrual period. Suitable preparation methods are described in Shamblott et al., Proc. Natl. Acad. Sci. USA 95:13726, 1998 and U.S. Pat. No. 6,090,622.

Briefly, genital ridges are rinsed with isotonic buffer, then placed into 0.1 mL 0.05% trypsin/0.53 mM sodium EDTA solution (BRL) and cut into <1 $mm^3$ chunks. The tissue is then pipetted through a 100 μL tip to further disaggregate the cells. It is incubated at 37° C. for ~5 min, then ~3.5 mL EG growth medium is added. EG growth medium is DMEM, 4500 mg/L D-glucose, 2200 mg/L mM sodium bicarbonate; 15% ES qualified fetal calf serum (BRL); 2 mM glutamine (BRL); 1 mM sodium pyruvate (BRL); 1000–2000 U/mL human recombinant leukemia inhibitory factor (LIF, Genzyme); 1–2 ng/ml human recombinant basic fibroblast growth factor (bFGF, Genzyme); and 10 μM forskolin (in 10% DMSO). In an alternative approach, EG cells are isolated using hyaluronidase/collagenase/DNAse. Gonadal anlagen or genital ridges with mesenteries are dissected from fetal material, the genital ridges are rinsed in PBS, then placed in 0.1 ml HCD digestion solution (0.01% hyaluronidase type V, 0.002% DNAse I, 0.1% collagenase type IV, all from Sigma prepared in EG growth medium). Tissue is minced and incubated 1 h or overnight at 37° C., resuspended in 1–3 mL of EG growth medium, and plated onto a feeder layer.

Ninety-six well tissue culture plates are prepared with a sub-confluent layer of feeder cells cultured for 3 days in modified EG growth medium free of LIF, bFGF or forskolin, inactivated with 5000 rad γ-irradiation. Suitable feeders are STO cells (ATCC Accession No. CRL 1503). ~0.2 mL of primary germ cell (PGC) suspension is added to each of the wells. The first passage is conducted after 7–10 days in EG growth medium, transferring each well to one well of a 24-well culture dish previously prepared with irradiated STO mouse fibroblasts. The cells are cultured with daily replacement of medium until cell morphology consistent with EG cells are observed, typically after 7–30 days or 1–4 passages.

Propagation of pPS Cells in the Absence of Feeder Cells pPS cells can be propagated continuously in culture, using a combination of culture conditions that promote proliferation without promoting differentiation.

Suitable source cells include established lines of pluripotent cells derived from tissue formed after gestation, including embryonic tissue (such as a blastocyst), or fetal tissue taken any time during gestation, typically but not necessarily before 10 weeks gestation. Non-limiting exemplars are established lines of hES or hEG cells. Also contemplated is use of the techniques of this disclosure during the initial establishment or stabilization of such cells, in which case the source cells would be primary pluripotent cells taken directly from the tissues listed. Also suitable as source cells are cells taken from an pPS cell population cultured previously in the absence of feeder cells.

In the absence of feeder cells, the pPS are plated onto a suitable culture substrate. Particularly suitable are extracellular matrix components, such as those derived from basement membrane or that may form part of adhesion molecule receptor-ligand couplings. A commercial preparation is available from Becton Dickenson under the name Matrigel®, and can be obtained in a Growth Factor Reduced formulation. Both formulations are effective. Matrigel® is a soluble preparation from Engelbreth-Holm-Swarm tumor cells that gels at room temperature to form a reconstituted basement membrane.

Other extracellular matrix components and component mixtures are suitable as an alternative. Depending on the cell type being proliferated, this may include laminin, fibronectin, proteoglycan, entactin, heparan sulfate, and the like, alone or in various combinations. Laminins are major components of all basal laminae in vertebrates, which interact with integrin heterodimers such as α6β1 and α6β4 (specific for laminins) and other heterodimers (that cross-react with other matrices). Using culture conditions illustrated in the examples, collagen IV supports hES cell growth without differentiation, while collagen I does not. Substrates that can be tested using the experimental procedures described herein include not only other extracellular matrix components, but also polyamines (such as polyornithine, polylysine), and other commercially available coatings.

The pluripotent cells are plated onto the substrate in a suitable distribution and in the presence of a medium that promotes cell survival, propagation, and retention of the desirable characteristics. All these characteristics benefit from careful attention to the seeding distribution. One feature of the distribution is the plating density. It has been found that plating densities of at least about 15,000 cells $cm^{-2}$ promote survival and limit differentiation. Typically, a plating density of between about 90,000 $cm^{-2}$ and about 170,000 $cm^{-2}$ is used.

Another feature is the dispersion of cells. The propagation of mouse stem cells involves dispersing the cells into a single-cell suspension (Robinson, Meth. Mol. Biol. 75:173, 1997 at page 177). In contrast, the passage of pPS cells in the absence of feeders benefits from preparing the pPS cells in small clusters. Typically, enzymatic digestion is halted before cells become completely dispersed (say, ~5 min with collagenase IV). The plate is then scraped gently with a pipette, and the cells are triturated with the pipette until they are suspended as clumps of adherent cells, about 10–2000 cells in size. The clumps are then plated directly onto the substrate without further dispersal. Naturally, a proportion of the cells may be separated as separate cells, but if the technique is done with sufficient care, 30%, 50% or even 75% of the total harvested cells will be in one of the small clumps. A cell preparation containing pPS cells is said to contain "clusters" if at least about 30% of the cells in the population is contained in adherent groups of at least 5 cells or more.

pPS cells plated in the absence of fresh feeder cells benefit from being cultured in a nutrient medium. The medium will generally contain the usual components to enhance cell survival, including isotonic buffer, essential minerals, and either serum or a serum replacement of some kind. Also beneficial is a medium that has been conditioned to supply some of the elements provided by feeder cells.

Conditioned medium can be prepared by culturing irradiated primary mouse embryonic fibroblasts (or another suitable cell preparation) at a density of ~5–6×10$^4$ cm$^{-2}$ in a serum free medium such as KO DMEM supplemented with 20% serum replacement and 4 ng/mL basic fibroblast growth factor (bFGF). The culture supernatant is harvested after ~1 day at 37° C. Devices for growing anchorage-dependent cells include T-flasks, roller bottles, gas-permeable bags, hollow fiber bioreactors, flat-bed bioreactors, and parallel plate bioreactors. If the cells are mobilized in a three-dimensional matrix they can be cultured in continuous stirred tank bioreactors or air-lift bioreactors.

As an alternative to primary mouse fibroblast cultures, conditioned medium can be prepared from a telomerized embryonic fibroblast cell line tested for its ability to condition medium appropriately (Examples 6 and 7). Another possible source is differentiated pPS cells with the morphological features of fibroblasts. pPS cells are suspension cultured as aggregates in differentiation medium using non-adherent cell culture plates (~2×10$^6$ cells/9.6 cm$^2$). After 2 days the aggregates are transferred into gelatin-coated plates, and fibroblast-like cells appear in clusters of 100–1000 cells in the mixed population after ~11 days. After brief collagenase treatment, the fibroblast-like cells can be collected under a microscope, passaged in mEF medium, and tested for their ability to condition ES medium.

As illustrated in the examples below, medium that has been conditioned for 1–2 days is typically used to support pPS cell culture for 1–2 days, and then exchanged. The medium can be used directly after conditioning, or it can be stored neat or as an extract (e.g., for 2 days, 7 days, or 14 days at 4° C.). The medium is typically used undiluted, but dilutions into fresh medium may also be possible, as may be ascertained by maintaining pPS cells under test conditions for 7 days or longer, and determining whether the cultures maintain morphological features and phenotypic markers characteristic of undifferentiated pPS cells.

If desired, conditioned medium can be supplemented before use with additional growth factors that benefit pPS cell culture. For hES, a growth factor like bFGF or FGF-4 is often used. For hEG, culture medium may be supplemented with a growth factor like bFGF, an inducer of gp130, such as LIF or Oncostatin-M, and perhaps a factor that elevates cyclic AMP levels, such as forskolin. Other types of pPS cells may benefit from other factors in the medium, such as stem cell factor (Steel factor, c-kit ligand), or IL-6. In some circumstances, it is beneficial to add growth factors such as bFGF or FGF-4 to the medium both before conditioning, and then again before using the medium to support the growth of pPS cells.

It is recognized that each of the conditions described here can be optimized independently, and certain combinations of conditions will prove effective upon further testing. Such optimization is a matter of routine experimentation, and does not depart from the spirit of the invention provided in this disclosure.

Characteristics of pPS Cells Grown Without Added Feeder Cells

Human ES cells have the characteristic morphological features of undifferentiated stem cells. In the two dimensions of a standard microscopic image, hES cells have high nuclear/cytoplasmic ratios in the plane of the image, prominent nucleoli, and compact colony formation with poorly discernable cell junctions. Cell lines can be karyotyped using a standard G-banding technique (available at many clinical diagnostics labs that provides routine karyotyping services, such as the Cytogenetics Lab at Oakland Calif.) and compared to published human karyotypes. It is desirable to obtain cells that have a "normal karyotype", which means that the cells are euploid, wherein all human chromosomes are present and are not noticeably altered.

hES and hEG cells can also be characterized on the basis of expressed cell markers. In general, the tissue-specific markers discussed in this disclosure can be detected using a suitable immunological technique—such as flow cytometry for membrane-bound markers, immunohistochemistry for intracellular markers, and enzyme-linked immunoassay, for markers secreted into the medium. The expression of protein markers can also be detected at the mRNA level by reverse transcriptase-PCR using marker-specific primers. See U.S. Pat. No. 5,843,780 for further details.

Stage-specific embryonic antigens (SSEA) are characteristic of certain embryonic cell types. Antibodies for SSEA-1, SSEA-3 and SSEA-4 are available from the Developmental Studies Hybridoma Bank of the National Institute of Child Health and Human Development (Bethesda Md.). Other useful markers are detectable using antibodies designated Tra-1-60 and Tra-1-81 (Andrews et al., *Cell Lines from Human Germ Cell Tumors*, in E. J. Robertson, 1987, supra). Mouse ES cells can be used as a positive control for SSEA-1, and as a negative control for SSEA-4, Tra-1-60, and Tra-1-81. SSEA-4 is consistently present on human embryonal carcinoma (hEC) cells. Differentiation of pPS cells in vitro results in the loss of SSEA-4, Tra-1-60, and Tra-1-81 expression and increased expression of SSEA-1. SSEA-1 is also found on hEG cells. pPS cells can also be characterized by the presence of alkaline phosphatase activity, which can be detected by fixing the cells with 4% paraformaldehyde, and then developing with Vector Red as a substrate, as described by the manufacturer (Vector Laboratories, Burlingame Calif.).

Another desirable feature of propagated pPS cells is a potential to differentiate into cells of all three germinal layers: endoderm, mesoderm, and ectoderm tissues. Pluripotency of hES cells can be confirmed by injecting approximately $3.0 \times 10^6$ cells into the rear leg muscles of 8–12 week old male SCID mice. The resulting tumors can be fixed in 4% paraformaldehyde and examined histologically after paraffin embedding at 8–16 weeks of development. Teratomas develop that demonstrate tissues of all three germ layers; for example cartilage, smooth muscle, or striated muscle (mesoderm); stratified squamous epithelium with hair follicles, neural tube with ventricular, intermediate, or mantle layers (ectoderm); and ciliated columnar epithelium and villi lined by absorptive enterocytes or mucus-secreting goblet cells (endoderm). Pluripotency of pPS cells can be further tested for differentiation into particular cell lines, according to procedures described later in this disclosure.

An exemplary preparation of hES cells grown in the absence of feeders is described in Example 1. At 19 days of culture, >80% of the cells stained positively for SSEA-4, Tra-1-60 and Tra-1-81, while <15% of the cells stained positively for SSEA-1.

Certain cell populations described in this disclosure are substantially undifferentiated, and can be passaged between multiple cultures to which no new feeder cells are added. It is recognized that during certain passages, some cells may differentiate (particularly when replated as single cells, or when large clusters are allowed to form). However, cultures typically reestablish a larger proportion of undifferentiated cells during the culture period. Of particular interest are cells that can be propagated in the feeder-free system for at least about 3 months. Optimally, the propagated cells will have a doubling time of no more than about 20–40 hours Where it is desirable to increase the replicative capacity of pPS cells, they can be telomerized by genetically altering them with a suitable vector, as illustrated above, so that they express telomerase reverse transcriptase (TERT). The catalytic component of human telomerase (hTERT) is provided in International Patent Publication WO 98/14592; mouse TERT is provided in WO 99/27113. Typically, the vector will comprise a TERT encoding region under control of a heterologous promoter that will promote transcription in the cell line. Transfection and expression of telomerase in human cells is described in Bodnar et al., Science 279:349, 1998 and Jiang et al., Nat. Genet. 21:111, 1999. Telomerase activity and hTERT expression can be determined using TRAP activity assay (Kim et al., Science 266:2011, 1997; Weinrich et al., Nature Genetics 17:498, 1997).

Other methods of immortalizing cells are also contemplated, such as genetically altering the cells with DNA encoding the SV40 large T antigen (U.S. Pat. No. 5,869,243, WO 97/32972), infecting with Epstein Barr Virus, introducing oncogenes such as myc and ras, introducing viral replication genes such as adenovirus E1a, and fusing cells having the desired phenotype with an immortalized cell line.

Differentiation of Propagated pPS Cells

Certain aspects of this invention relate to taking pPS cells from feeder-free cultures, and differentiating them into committed precursor cells or terminally differentiated cells.

Differentiation of the pPS can be initiated by first forming embryoid bodies. General principles in culturing embryoid bodies is reported in OShea, Anat. Rec. (New Anat. 257:323, 1999). pPS cells are cultured in a manner that permits aggregates to form, for which many options are available: for example, by overgrowth of a donor pPS cell culture, or by culturing pPS cells in culture vessels having a substrate with low adhesion properties which allows EB formation. Embryoid bodies can also be made in suspension culture. pPS cells are harvested by brief collagenase digestion, dissociated into clusters, and plated in non-adherent cell culture plates. The aggregates are fed every few days, and then harvested after a suitable period, typically 4–8 days. The cells can then be cultured in a medium and/or on a substrate that promotes enrichment of cells of a particular lineage. The substrate can comprise matrix components such as Matrigel® (Becton Dickenson), laminin, collagen, gelatin, or matrix produced by first culturing a matrix-producing cell line (such as a fibroblast or endothelial cell line), and then lysing and washing in such a way that the matrix remains attached to the surface of the vessel. Embryoid bodies comprise a heterogeneous cell population, potentially having an endoderm exterior, and a mesoderm and ectoderm interior.

Scientists at Geron Corporation have discovered that pPS cells can be differentiated into committed precursor cells or terminally differentiated cells without forming embryoid bodies or aggregates as an intermediate step. Briefly, a suspension of undifferentiated pPS cells is prepared, and then plated onto a solid surface that promotes differentiation. Suitable substrates include glass or plastic surfaces that are adherent, for example, by coating with a polycationic substance, such as a polyamine or polyornithine, or matrix components such as laminin or fibronectin. In some circumstances, differentiation is further promoted by withdrawing serum, serum replacement, or other components of the medium, such as growth factors, mitogens, leukocyte inhibitory factor (LIF), or basic fibroblast growth factor (bFGF). Differentiation may also be promoted by adding a medium component that promotes differentiation towards the desired cell lineage, or inhibits the growth of cells with undesired characteristics. For example, to generate cells committed to neural or glial lineages, the medium can include any of the following factors or medium constituents in an effective combination: Brain derived neurotrophic factor (BDNF), neutrotrophin-3 (NT-3), NT-4, epidermal growth factor (EGF), ciliary neurotrophic factor (CNTF), nerve growth factor (NGF), retinoic acid (RA), sonic hedgehog, FGF-8, ascorbic acid, forskolin, fetal bovine serum (FBS), and bone morphogenic proteins (BMPs).

Adjunct techniques useful in the derivation of particular cell types can be inferred by analogy from papers describing other types of precursors. General principals for obtaining tissue cells from pluripotent stem cells are reviewed in Pedersen (Reprod. Fertil. Dev. 6:543, 1994), and U.S. Pat. No. 6,090,622. For neural progenitors, neural restrictive cells and glial cell precursors, see Bain et al., Biochem. Biophys. Res. Commun. 200:1252, 1994; Trojanowski et al., Exp. Neurol. 144:92, 1997; Wojcik et al., Proc. Natl. Acad. Sci. USA 90:1305–130; and U.S. Pat. No. Nos. 5,851,832, 5,928,947, 5,766,948, and 5,849,553. For cardiac muscle and cardiomyocytes see Chen et al., Dev. Dynamics 197:217, 1993 and Wobus et al., Differentiation 48:173, 1991. For hematopoietic progenitors, see Burkert et al., New Biol. 3:698, 1991 and Biesecker et al., Exp. Hematol. 21:774, 1993. U.S. Pat. No. 5,773,255 relates to glucose-responsive insulin secreting pancreatic beta cell lines. U.S. Pat. No. 5,789,246 relates to hepatocyte precursor cells. Other progenitors of interest include but are not limited to chondrocytes, osteoblasts, retinal pigment epithelial cells, fibroblasts, skin cells such as keratinocytes, dendritic cells, hair follicle cells, renal duct epithelial cells, smooth and skeletal muscle cells, testicular progenitors, and vascular endothelial cells.

Scientists at Geron Corporation have discovered that culturing pPS cells or embryoid body cells in the presence of ligands that bind growth factor receptors promotes enrichment for neural precursor cells. The growth environment may contain a neural cell supportive extracellular matrix, such as fibronectin. Suitable growth factors include but are not limited to EGF, bFGF, PDGF, IGF-1, and antibodies to receptors for these ligands. The cultured cells may then be optionally separated on the basis of whether they express a marker such as A2B5. Under the appropriate circumstances, populations of cells enriched for expression of the A2B5 marker may have the capacity to generate both neuronal cells (including mature neurons), and glial cells (including astrocytes and oligodendrocytes. Optionally, the cell populations are further differentiated, for example, by culturing in a medium containing an activator of cAMP. Markers of interest include but are not limited to β-tubulin III or neurofilament, characteristic of neurons; glial fibrillary acidic protein (GFAP), present in astrocytes; galactocerebroside (GalC) or myelin basic protein (MBP); characteristic of oligodendrocytes; OCT-4, characteristic of undifferentiated hES cells; Nestin or Musashi, characteristic of neural precursors and other cells; and both A2B5 and NCAM, which appear on populations of differentiated from pPS cells capable of forming both neuronal cells and glial cells.

Scientists at Geron Corporation have also discovered that culturing pPS cells or embryoid body cells in the presence of a hepatocyte differentiation agent promotes enrichment for hepatocyte-like cells. The growth environment may contain a hepatocyte supportive extracellular matrix, such as collagen or Matrigel®. Suitable differentiation agents include various isomers of butyrate and their analogs, exemplified by n-butyrate. The cultured cells are optionally cultured simultaneously or sequentially with a hepatocyte maturation factor, such as an organic solvent like dimethyl sulfoxide (DMSO); a maturation cofactor such as retinoic acid; or a cytokine or hormone such as a glucocorticoid, epidermal growth factor (EGF), insulin, transforming growth factors (TGF-α and TGF-β), fibroblast growth factors (FGF), heparin, hepatocyte growth factors (HGF), interleukins (IL-1 and IL-6), insulin-like growth factors (IGF-I and IGF-II), and heparin-binding growth factors (HBGF-1). Hepatocyte lineage cells differentiated from pPS cells will typically display at least three of the following markers: $α_1$-antitrypsin (AAT) synthesis, albumin synthesis, asialoglycoprotein receptor (ASGR) expression, absence of α-fetoprotein, evidence of glycogen storage, evidence of cytochrome p450 activity, and evidence of glucose-6-phosphatase activity.

Cell types in mixed cell populations derived from pPS cells can be recognized by characteristic morphology and the markers they express. For skeletal muscle: myoD, myogenin, and myf-5. For endothelial cells: PECAM (platelet endothelial cell adhesion molecule), Flk-1, tie-1, tie-2, vascular endothelial (VE) cadherin, MECA-32, and MEC-14.7. For smooth muscle cells: specific myosin heavy chain. For cardiomyocytes: GATA-4, Nkx2.5, cardiac troponin I, α-myosin heavy chain, and ANF. For pancreatic cells, pdx and insulin secretion. For hematopoietic cells and their progenitors: GATA-1, CD34, β-major globulin, and β-major globulin like gene βH1.

Isolating mRNA and Making Amplified Copies

Undifferentiated pPS cells grown with feeder cells or from feeder-free cultures can be used to prepare mRNA and cDNA libraries that reflect the gene expression patterns of these cells. mRNA and cDNA can also be made from differentiated cells, and used to produce subtraction libraries enriched for transcripts that are up- or down-regulated during differentiation.

Preparing a cDNA library will typically involve isolating mRNA from pPS cells or their differentiated progeny; making a polynucleotide copy of the mRNA, and producing a library that contains the polynucleotide copies in a form that can be replenished. Typically, the polynucleotide copy is cDNA generated by a reverse transcriptase reaction from the mRNA template, but any other type of copy that retains the sequence of the original mRNA population can be used.

Optionally, polynucleotide copies from different sources (for example, pPS and differentiated cells) are subtracted to produce a library enriched for copies differentially expressed between the two populations. The selected polynucleotide copies are typically engineered into a cloning vector, but any way of reproducing the copies in a vector, a host cell, or by chemical means is understood to be equivalent.

By way of illustration, hES cells in feeder-free culture are released from the matrix using collagenase and collected by centrifugation, or lysed directly in culture using a suitable solvent. Total RNA is prepared from the cells by an appropriate combination of standard techniques (e.g., acid phenol/chloroform extraction, centrifugation through CsCl, binding to an oligo-dT matrix, etc.; see Sambrook et al., supra). As illustrated in Example 8, total RNA can be isolated from harvested hES cells by lysing the cells in a solution of guanidinium isothiocyanate and binding RNA in the suspension to a suitable matrix (U.S. Pat. No. 5,234,809), such as an RNeasy® spin column (Qiagen Inc., Valencia Calif.). Total RNA is eluted from the matrix, and then poly $A^+$ mRNA is obtained by binding to Oligotex™ beads having bound $dC_{10}T_{30}$ oligonucleotides. The adherent fraction is collected in a low salt buffer, and can be used to prepare a cDNA library.

A variety of methodologies is available to convert mRNA into double-stranded cDNA. Products include primary libraries, designed to represent the starting mRNA population; subtracted libraries, in which mRNA species common to two or more different mRNA population are reduced in the final cDNA preparation to enrich for mRNA preferentially expressed in one population; normalized libraries, in which the relative abundance of independent mRNAs is balanced towards equal representation; and full-length biased libraries, in which the production of cDNA is optimized to produce a high frequency of cDNA that include the entire coding sequence of the original mRNA.

The first reaction in these methods is typically the conversion of mRNA into a single-stranded cDNA using a template-dependent reverse-transcription reaction primed with oligo-dT or random hexamer primers. This reaction is catalyzed by a reverse-transcriptase, a class of enzymes readily obtainable from commercial suppliers. Exemplary is SuperScript II™ (Life Technologies Inc., Bethesda), a modified version of reverse transcriptase in which RNAse H activity of the native enzyme has been reduced, thereby increasing the frequency with which full-length first strand cDNA is produced. Oligo-dT primers are typically modified on the 5' end to incorporate a restriction endonuclease recognition sequence to facilitate cloning. Often, a methylated version of one nucleotide triphosphate is included in the first strand reaction. Thus the final cDNA is protected from digestion with restriction endonucleases typically used to restrict the final product.

Conversion of the single strand cDNA product of the reverse transcriptase reaction to double-strand cDNA can be accomplished by several means. Typically, the first strand cDNA is adapted to allow the priming of complementary strand synthesis by a suitable DNA polymerase. The SMART™ technology (ClonTech, Palo Alto, Calif.) utilizes a strand switch oligonucleotide that primes second strand synthesis from terminal cytosine residues at the terminus of the first strand product. Other techniques for adapting the first strand cDNA product include introduction of a homopolymeric tail using terminal deoxynucleotidyl transferase followed by second strand priming with the complementary homopolymer, or the ligation of an appropriate oligonucleotide followed by second strand priming with a primer complementary to the ligated oligo. With this latter approach, the ligated oligonucleotide and its complement can be designed to include restriction endonuclease recognition sequences that facilitate cloning.

In one illustration, the action of RNAse H is used to introduce nicks into the RNA/DNA duplex, which then become suitable as priming sites for DNA polymerases, such as Pol1 from E. coli. This method is efficient, but sequence information may be lost from the 5' end of the cDNA, since the priming RNA overlying the 5' end (the terminus opposite of the polyA+ site in the original mRNA) will be lost with subsequent processing of the double-stranded cDNA. Alternatively, double-stranded DNA in which the 5' sequence information is preserved involves ligation of an oligonucleotide primer to the 3' end of first strand cDNA. This ligation reaction is catalyzed by T4 RNA ligase, an enzyme capable of joining the terminal 5' phosphate of a single strand oligonucleotide with the 3'-hydroxyl of the first-strand cDNA product. The oligonucleotide used is synthesized so as to provide a 5'-terminal phosphate, to allow ligation to the cDNA, and a 3'-blocking group, such as an amino- or dideoxy-derivatives, to prevent self-concatamerization. This oligonucleotide also encodes restriction endonuclease recognition sequences that adapt sites appropriate for subsequent cloning into vectors. Following ligation of the oligonucleotide to the first strand cDNA products, second strand cDNA synthesis is primed with an oligonucleotide complementary to the ligated oligo using an appropriate DNA polymerase activity, such as thermostable polymerases. Sequence example: first strand cDNA ligation oligo 5'P-AGGTCGACGAGAGAG-3'NH-X (SEQ. ID NO:1), where P=phosphate, NH-X=amine blocking group; complementary oligo 5'OH-CTCTCTCGTCGACCT-OH-3' (SEQ. ID NO:2), where —OH=hydroxyl group.

Certain procedures can be used to increase the proportion of full-length cDNA in the sample. Suitable for this purpose is technology developed at the RIKEN Institute, Japan (Carninci et al., Methods Enzymol. 303:19, 1999; Itoh et al., Genome Res.9:463, 1999; see also International Patent Application WO 98/20122). mRNA is adapted by adding a biotin to the 7-methyl G cap structure at the 5'-end of the mRNA. Production of the first strand cDNA is achieved as already described, and the cDNA/mRNA hybrid is treated with RNAse I, which degrades single stranded mRNA. mRNA that is not protected by hybridization to a full-length cDNA is hydrolyzed, while full-length cDNA/mRNA hybrids remain. The hybrids are purified using streptavidin-coated beads that bind the biotin at the 5' cap, and converted into double-strand cDNA using standard techniques. The resulting proportion of full-length cDNA in the sample is typically much higher than what is present in libraries made by traditional methods. Several commercial vendors offer services to produce full-length biased cDNA, including Life Technologies Inc. (Bethesda, Md.) and Seqwright Inc. (Houston, Tex.).

Subtracted libraries provide an enriched source of genes whose expression levels differ between two mRNA populations. Methods for making subtracted libraries typically involve amplifying mRNA obtained from pPS cells (for example, by forming a cDNA population as already described); amplifying mRNA obtained from differentiated cells; incubating the two pools together under conditions that permit polynucleotides amplified from mRNA expressed in both the pPS cells and the differentiated cells to cross-hybridize; and then recovering amplified polynucleotides that have not cross-hybridized.

In a similar fashion, subtracted libraries can be made from other combinations of mRNA isolates—for example, pPS cells from feeder cultures vs. pPS cells in feeder-free culture; partially differentiated cells vs. terminally differentiated cells; or differentiated cell populations of two or more different lineages. In another example, cDNA from pPS cells differentiated in monolayer culture (by plating on a matrix or other substrate that promotes differentiation, or by treating with agents such as DMSO or retinoic acid) is subtracted from cDNA from pPS cells grown in feeder-free culture, to correct for the proportion of differentiated cells that form on the periphery around each colony. Subtraction libraries can also be made to ascertain the effect of a compound or change in culture conditions on expression patterns in undifferentiated pPS cells, or their differentiated progeny. Amplified mRNA is made from cells exposed to the compound or condition, and subtracted with amplified mRNA from control cells. The library will thereby be enriched for transcripts that are upregulated or downregulated as a result of the change.

The preparation of subtraction libraries can be illustrated as follows: two independent mRNA pools are prepared, one termed the tester and the other the driver. In this illustration, they are converted into an appropriate form, often single stranded cDNA (one of the pools in sense orientation, the other in antisense orientation), and then mixed to allow hybridization. Transcripts that are common to both mRNA populations will form hybrids, while those transcripts that are found only in one pool, or are expressed at substantially higher levels in one pool, remain unhybridized. The hybrids are then removed, typically by partitioning over chromatographic columns or by retrieval using specific biochemical systems such as streptavidin/biotin. The remaining single-strand sequences, now enriched for genes that are more highly expressed in the tester mRNA pool, are cloned into a suitable vector. Many variations of subtractive library production have been developed. A method which combined the features of subtractive hybridization incorporating normalization is commercially available (Suppressive Subtractive Hybridization (SSH), ClonTech, Palo Alto, Calif.).

Preparing Recombinant Expression Libraries

Double-stranded cDNA made by these techniques can be engineered into a variety of cloning vectors. Suitable vector systems include bacterial plasmids and lambda bacteriophage for cloning in bacterial hosts. When the cDNA is produced with endonuclease-restricted termini, cloning is often accomplished by ligation with correspondingly restricted vector DNA. Plasmid libraries are favored for sequence analysis, since the individual clones can be readily processed by high-throughput purification and PCR amplification protocols.

In certain embodiments of the invention, the cloning vector is also an expression vector, designed so that isolated plaques can be transfected into cells to obtain the gene product. Accordingly, the amplified transcripts are placed in the vector under control of transcription and translation control elements. For instance, the plasmid pCMVSPOR™ 6.0 (Life Technologies Inc., Bethesda Md.) contains SP6 and T7 viral RNA polymerase promoters on opposite flanks of the multiple cloning site, allowing for the transcription of sense or antisense strands of cloned cDNA. As well, a CMV promoter cassette confers in vivo transcription when introduced into mammalian host cells. Thus, cDNA inserted into such vectors can be tested for expression in a variety of host cells, including pPS cells. This vector also features lambda phage attachment sequences flanking the multiple cloning site, making them compatible with Life Technologies Gateway™ vectors. The Gateway™ system includes vectors that are specifically modified with sequences that allow for the transfer of cloned sequences between vectors by use of a enzyme cocktail of lambda phage and *E. coli* recombinase activities. This obviates the need to use restriction enzyme digestions when transferring sequences between vectors.

Of particular interest are libraries optimized for expression of the cDNA in pluripotent stem cells. Methylation patterns and other regulatory control mechanisms in embryonic cells can suppress transcription of genes under control of promoters such as CMV, which are active in most other eukaryotic cell types. It has been discovered that promoters for house-keeping genes active in pPS cells may be effective for controlling transcription of artificially introduced encoding regions. As illustrated in Example 9, an appropriate promoter can be selected experimentally using reporter constructs comprising test promoter sequences, a reporter gene such as green fluorescent protein or β-galactosidase, and a drug resistance gene. An appropriate promoter will have the characteristic of causing expression of the reporter gene, without substantially increasing the proportion of cells lost to differentiation. Using this selection strategy, the promoter for phosphoglycerate kinase (PGK) has been determined as effective for construction of libraries expressible in pPS cells.

Characterizing Recombinant Expression Libraries cDNA libraries can be characterized by several criteria. A simple and direct estimation of the length of cDNAs can be made by digesting plasmid preparations from individual clones with restriction enzymes that release the cDNA insert. The digestion products can be sized by electrophoresis using agarose gels, and a median cDNA insert length can be calculated. Certain characteristics of expression libraries can be achieved by comparing sequences generated from the 5' end of individual cDNA clones with sequences found in public databases. Polynucleotide isolates and cloned inserts of this invention can be sequenced using any suitable method in the art. Exemplary are PCR-based sequencing methods that form fluorescent products to be resolved using automated DNA sequencers. The plasmid DNA and a sequencing primer are reacted under PCR reaction conditions which include fluorescently-labeled dideoxynucleotide triphosphates. The resulting reaction products are resolved on an appropriate DNA sequencer, such as the ABI 377 (Perkin-Elmer Biosystems, Foster City Calif.). The fluorescence signal is detected, converted into raw sequence information and processed. DNA sequencing services based substantially on these methods are available commercially from such companies as Lark Technologies, Houston, Tex.; and Incyte Genomics, Palo Alto, Calif. Having obtained the open reading frame of the mRNA encoding sequence, the amino acid sequence of the protein gene product can normally be determined without further experimentation by translating the encoding sequence according to the genetic code.

The sequence data provides a general estimate of the diversity of the cDNA library, based on the number of independent genes represented. For instance, comparing the cDNA sequences to the UNIGENE collection (National Center for Biotechnology Information internet website) allows assignment of a unique cluster identifier for most sequences. By comparing the number of assigned cluster identifiers to the total number of cDNAs evaluated, an estimate of the clone diversity can be achieved.

Libraries that represent less complex mRNA sources have relatively fewer independent gene sequences represented in a given number of cDNAs compared to libraries made from more complex mRNA sources. In certain embodiments of this invention, mRNA preparations, cDNA preparations, and libraries in cloning vectors contain sequences representaing at least 100, 1,000, 10,000, or even 50,000 genes expressed at the mRNA level in pPS cells or their differentiated progeny.

Libraries can also be characterized on the basis of whether they contain transcripts from cells of a single genotype. Crude sequence data from different plaques are matched with databases of human sequences, and sequences of other species that are also suspected of being present. The library is referred to as "essentially free" of cDNA of other species, vertebrates, mammals, and different genotypes of the same species if less than about 1% of the transcript copies in the library have sequences establishing that they did not originate from the genotype from which the cDNA library is desired. Using the feeder-free culture systems described in this disclosure, the degree of contamination of pPS cell libraries with foreign transcripts can be less than 0.2%, 0.05%, 0.01%, or 0.001%, depending on the number of passages from the last culturing of the pPS cells on a feeder layer.

The 5' sequences from cDNAs can also be compared to collections of annotated full-length mRNA sequences to determine the proportion of cDNAs that represent full-length sequences. In this context, full-length sequences can be defined as those that include the initiator methionine codon for an encoded protein. For example, 5' sequence reads can be compared to the REFSEQ collection (GenBank) using an appropriate search program such as BLAST. For those cDNA sequences that match to a REFSEQ entry, an evaluation of the sequence alignment can indicate whether the cDNA sequence includes the initiator methionine for the protein encoded by the REFSEQ entry and thus the proportion of full-length cDNAs can be estimated. Since the REFSEQ collection is annotated to indicate the estimated size of full-length mRNA, this analysis can be evaluated further to determine the percentage of full-length cDNAs that correspond to mRNAs of a particular size. For example, it is possible to compare the percentage of full-length cDNAs that correspond to mRNAs of less than 1 kb in length, versus the percentage of full-length cDNAs that correspond to mRNAs greater than 1 kb in length.

Depending on the method by which such products are derived, the proportion of cDNA that comprises the entire encoding region of the corresponding mRNA can be at least 15%, 30%, and sometimes 50% of the polynucleotide or vectors in the preparation. The median length of the insert can be at least ~0.5 kb, 1 kb, 2 kb, or 4 kb, depending on the method used to obtain and select the double-stranded cDNA preparation.

Use of information from expression libraries

Once the sequence of an mRNA or cDNA from pPS cells or their differentiated progeny has been determined, it can be used in the manufacture of polynucleotides that contain such sequences, polypeptides they encode, and antibody specific for the polypeptides.

Polynucleotides are manufactured according to techniques of nucleic acid chemistry for any suitable purpose in research, diagnostic, or therapeutic applications. Nucleotide sequences can be modified to remove segments of the native coding region, add additional encoding sequence, or introduce mutations and other changes for any desirable purpose. Substantially identical polynucleotides or polynucleotide fragments hybridize under stringent conditions to cDNA in an expression library from pPS cells or their differentiated progeny, in preference to other nucleotide sequences contained in the human genome or expressed in other cell types. Typical conditions of high stringency for the binding of a probe of about 100 base pairs and above is a hybridization reaction at 65° C. in 2×SSC, followed by repeat washes at 0.1×SSC. In certain embodiments, a segment of the manufactured polynucleotide is at least about 80%, 90%, 95%, or 100% identical to a sequence or part of a sequence determined for a cDNA obtained as described in this disclosure. The length of consecutive residues in the identical or homologous sequence compared with the exemplary sequence can be at least about 15, 30, 50, 75, 100, 200 or 500 residues in order of increasing preference.

Based on the desired nucleic acid sequence, polynucleotides can be manufactured according to any suitable technique. Oligonucleotides of less than ~50 base pairs are conveniently prepared by chemical synthesis, either through a commercial service or by a known synthetic method, such as the triester method or the phosphite method. A suitable method is solid phase synthesis using mononucleoside phosphoramidite coupling units (Hirose et al., *Tetra. Lett.* 19:2449–2452, 1978; U.S. Pat. No. 4,415,732). Polynucleotides with modified backbones can be prepared, such as those described in U.S. Pat. Nos. 5,578,718; 5,541,307; 5,378,825. Preparation of peptide nucleic acids is described in U.S. Pat. Nos. 5,539,082, 5,766,855, 5,786,461, and EP Application 97918549.2.

Alternatively, polynucleotides of this invention can be manufactured by PCR amplification using a template with the desired sequence. Oligonucleotide primers spanning the desired sequence are annealed to the template, elongated by a DNA polymerase, and then melted at higher temperature so that the template and elongated oligonucleotides dissociate. The cycle is repeated until the desired amount of amplified polynucleotide is obtained (U.S. Pat. Nos. 4,683,195 and 4,683,202). Suitable templates include expression libraries prepared from pPS cells or their progeny, or a library from any tissue where the corresponding gene is expressed in humans. Production scale amounts of large polynucleotides are conveniently obtained by inserting the desired sequence into a suitable cloning vector, and either reproducing the clone, or transfecting the sequence into a suitable host cell. Techniques for nucleotide cloning are given in Sambrook, Fritsch & Maniatis (supra) and in U.S. Pat. No. 5,552,524. Polynucleotides can be purified by standard techniques in nucleic acid chemistry, such as phenol-chloroform extraction, agarose gel electrophoresis, and other techniques known in the art, adapted according to the source.

The sequence data of an mRNA or cDNA of this invention can also be used to manufacture peptides that comprise a sequence contained in an encoding region. Amino acid sequences can be modified to remove or add segments, or introduce mutations and other changes for any desirable purpose. Substantially identical polypeptides or polypeptide fragments share an epitope recognized by an antibody specific for a protein encoded in a cDNA of an expression library from pPS cells or their differentiated progeny, in preference to other nucleotide sequences contained in the human genome or expressed in other cell types. In certain embodiments, the peptides are 60%, 80%, 90%, 95%, or 100% identical to a peptide or peptide fragment encoded in the mRNA or cDNA, in order of increasing preference. The length of the identical or homologous sequence compared with the prototype polypeptide can be about 7, 10, 15, 25, 50 or 100 residues in order of increasing preference, up to the length of the entire protein.

Polypeptides and their variants can be manufactured according to any suitable technique. Short polypeptides can be prepared by solid-phase chemical synthesis. The principles of solid phase chemical synthesis can be found in Dugas & Penney, Bioorganic Chemistry, Springer-Verlag NY pp 54–92 (1981), and U.S. Pat. No. 4,493,795. Automated solid-phase peptide synthesis can be performed using devices such as a PE-Applied Biosystems 430A peptide synthesizer (commercially available from Applied Biosystems, Foster City Calif.).

Longer polypeptides are conveniently manufactured by translation in an in vitro translation system, or by expression in a suitable host cell. To produce an expression vector, a polynucleotide encoding the desired polypeptide is operatively linked to control elements for transcription and translation, and then transfected into a suitable host cell, including prokaryotes such as E. coli, eukaryotic microorganisms such as the yeast Saccharomyces cerevisiae, or higher eukaryotes, such as insect or mammalian cells. A number of expression systems suitable for producing the peptides of this invention are described in U.S. Pat. No. 5,552,524. Expression cloning is available from such commercial services as Lark Technologies, Houston Tex. Following production, the protein is typically purified by standard methods in protein chemistry in appropriate combination, which may include ion exchange chromatography, affinity chromatography, or HPLC.

Polyclonal and monoclonal antibody specific for polypeptides encoded by mRNA and cDNA of this invention can be obtained by determining amino acid sequence from a protein encoding region in an expression library, and immunizing an animal or contacting an immunocompetent cell or particle with a protein containing the determined sequence.

Production of monoclonal antibody is described in such standard references as Harrow & Lane (1988), U.S. Pat. Nos. 4,491,632, 4,472,500 and 4,444,887, and Methods in Enzymology 73B:3 (1981). Other methods of obtaining specific antibody molecules (optimally in the form of single-chain variable regions) involve contacting a library of immunocompetent cells or viral particles with the target antigen, and growing out positively selected clones. See Marks et al., New Eng. J. Med. 335:730, 1996, International Patent Publications WO 94/13804, WO 92/01047, WO 90/02809, and McGuiness et al., Nature Biotechnol. 14:1449, 1996. By positively selecting using pPS of this disclosure, and negatively selecting using cells bearing more broadly distributed antigens (such as differentiated embryonic cells) or adult-derived stem cells, the desired specificity can be obtained.

Polynucleotides, polypeptides, and antibody derived from sequence data obtained from mRNA or cDNA of this invention have a number of important commercial applications. For example, genes or proteins that are expressed in pPS cells but decrease during differentiation can be used as molecular markers of the undifferentiated state. Reagents corresponding to these markers, such as antibodies, can be used to eliminate undifferentiated pPS cells from a population of differentiated cells by immunoaffinity isolation or complement-mediated lysis. Genes or proteins that increase expression levels during differentiation can be used in a similar manner to purify, enrich, remove or eliminate specific cell types derived from pPS cells. These markers may serve as indicators of broad classes of cell differentiation, such as genes or proteins expressed in mesodermal, endodermal or ectodermal lineages, or may serve as specific markers of a confined spectrum of highly differentiated cell types.

Genes that are upregulated during expression may also be useful to influence the differentiation of pPS cells into specific lineages. For instance, the forced expression in undifferentiated pPS cells of transgenes encoding transcription factors, growth factors, receptors and signaling molecules can be tested for an ability to influence differentiation into specific cell lineages.

The examples that follow are provided by way of further illustration, and are not meant to imply any limitation in the practice of the claimed invention.

EXAMPLES

Example 1

Feeder-Free Passage of hES Cells

In this experiment, undifferentiated hES cells that had been maintained on primary mouse embryonic feeder cells were harvested, and then maintained in the absence of feeders. The culture wells were coated with Matrigel®, and the cells were cultured in the presence of conditioned nutrient medium obtained from a culture of irradiated primary fibroblasts.

Preparation of Conditioned Media (CM) From Primary Mouse Embryonic Fibroblasts (mEF):

Fibroblasts were harvested from T150 flasks by washing one time with $Ca^{++}/Mg^{++}$ free PBS and incubating in 1.5–2 mL trypsin/EDTA (Gibco) for about 5 min. After the fibroblasts detached from the flask, they were collected in mEF media (DMEM+10% FBS). The cells were irradiated at 4000 rad (508 sec at 140 kV: shelf setting 6 in a Torrex generator), counted and seeded at about 55,000 cells $cm^{-2}$ in mEF media (525,000 cells/well of a 6 well plate). After at least 4 hours the media were exchanged with SR containing ES media, using 3–4 mL per 9.6 cm well of a 6 well plate. Conditioned media was collected daily for feeding of hES cultures. Alternatively, medium was prepared using mEF plated in culture flasks, exchanging medium daily at 0.3–0.4 mL $cm^{-2}$. Before addition to the hES cultures, the conditioned medium was supplemented with 4 ng/mL of human bFGF (Gibco). Fibroblasts cultures were used in this system for about 1 week, before replacing with newly prepared cells.

Matrigel® Coating:

Growth Factor Reduced Matrigel® or regular Matrigel® (Becton-Dickinson, Bedford Mass.) was thawed at 4° C. The Matrigel® was diluted 1:10 to 1:500 (typically 1:30) in cold KO DMEM. 0.75–1.0 mL of solution was added to each 9.6 $cm^2$ well, and incubated at room temp for 1 h. The coated wells were washed once with cold KO DMEM before adding cells. Plates were used within 2 h after coating, or stored in DMEM at 4° C. and used within ~1 week.

Human ES Culture:

Undifferentiated hES colonies were harvested from hES cultures on feeders as follows. Cultures were incubated in ~200 U/mL collagenase IV for about 5 minutes at 37° C. Colonies were harvested by picking individual colonies up with a 20 µL pipet tip under a microscope or by scraping and dissociating into small clusters in conditioned medium (CM). These cells were then seeded onto Matrigel® in conditioned media at 15 colonies to each 9.6 $cm^2$ well (if 1 colony is ~10,000 cells, then the plating density is ~15,000 cells $cm^{-2}$).

The day after seeding on Matrigel®, hES cells were visible as small colonies (~100–2,000 cells) and there were single cells in-between the colonies that appeared to be differentiating or dying. As the hES cells proliferated, the colonies became quite large and very compact, representing the majority of surface area of the culture dish. The hES cells in the colonies had a high nucleus to cytoplasm ratio and had prominent nucleoli, similar to hES cells maintained on feeder cells. At confluence, the differentiated cells in between the colonies represented less than 10% of the cells in the culture.

Six days after seeding, the cultures had become almost confluent. The cultures were split by incubating with 1 mL ~200 U/mL Collagenase IV solution in KO DMEM for ~5 minutes at 37 ° C. The collagenase solution was aspirated, 2 mL hES medium was added per well, and the hES cells were scraped from the dish with a pipette. The cell suspension was transferred to a 15 mL conical tube, brought up to a volume of 6 mL, and gently triturated to dissociate the cells into small clusters of 10–2000 cells. The cells were then re-seeded on Matrigel® coated plates in CM, as above. Cells were seeded at a 1:3 or 1:6 ratio, approximately 90,000 to 170,000 cells $cm^{-2}$, making up the volume in each well to 3 mL. Medium was changed daily, and the cells were split and passaged again at 13 d and again at 19 d after initial seeding.

On day 19 after initial seeding, cells were harvested and evaluated for surface marker expression by immunofluorescence cell cytometry, using labeled antibodies specific for cell surface markers. The results from this experiment are as follows:

TABLE 1

Phenotype of hES Cells Grown in the Absence of Feeder Cells

| Marker | Specificity | Percentage of Cells Staining |
| --- | --- | --- |
| SSEA-4 | undifferentiated cells | 92% |
| Tra-1-60 | undifferentiated cells | 92% |
| Tra-1-81 | undifferentiated cells | 83% |
| SSEA-1 | differentiated cells | 12% |

For the hES cells maintained in the absence of feeders, a high percentage express SSEA-4, Tra-1-60 or Tra-1-81. These 3 markers are expressed on undifferentiated human ES cells that are maintained on feeders (Thomson et al., 1998). In addition, there is very little expression of SSEA-1, a glycolipid that is not expressed(or expressed at low levels) on undifferentiated ES cells. Immunohistochemical evaluation of SSEA-4, Tra-1-60 and Tra-1-81 indicates that the expression of these markers is localized to the ES colonies, not the differentiated cells in between the colonies.

Cultures of hES cells were grown in the absence of feeder cells for 26 days after initial seeding, with no apparent change in the proliferative capacity or phenotype.

Example 2

Characteristics of hES Cells Grown on Matrigel® hES cells grown in the absence of feeder cells according to Example 1 are further characterized as follows:

PCR analysis of the expression of OCT-4. OCT-4 is a member of the POU transcription factor family; its expression is associated with an undifferentiated phenotype in ES cells and in the pre-implantation embryo.

Teratoma analysis. hES cells are injected into SCID/beige mice to assess teratoma formation, a defining feature of ES cells. One, 5, or 10 million cells(typically 5 million cells) are injected intramuscularly into SCID/beige mice. One to four months after injection, teratomas are harvested and fixed for histological evaluation for the presence of cell types from all three germ layers.

The karyotype of the cells is assessed by G-banding.

The cells are assessed by standard in vitro techniques for the ability to make embryoid bodies and differentiated cells. The differentiated cells are evaluated by immunocytochemical and RNA expression to determine the ability to make cells with the characteristics of mesoderm, endoderm and ectoderm lineages.

The hES are also evaluated for conditions that permit cryopreservation. The cells are frozen in standard medium supplemented with 10% DMSO and 20–30% SR in a controlled rate freezer. Modifications are made to this procedure as necessary to help preserve viability, the objective being to achieve conditions that permit hES cell proliferation after thawing.

Example 3

Matrigel® and Laminin Support Feeder-Free Growth of hES Cells

In this experiment, the growth of the hES cells was followed on different matrix components, in medium conditioned using primary mouse embryonic fibroblasts (mEF). hES cultures were initially harvested from feeder cell cultures maintained in ES medium (80% knockout DMEM (Gibco BRL, Rockville, Md.), 20% knockout serum replacement (Gibco BRL, Rockville, Md.), 1% Non-essential amino acids (Gibco BRL, Rockville, Md), 1 mM L-glutamine (Gibco), 0.1 mM β-mercaptoethanol (Sigma, St. Louis, Mo.), supplemented with 4 ng/mL recombinant human basic fibroblast growth factor (hbFGF; Gibco). Cultures were passaged by incubation in ~200 U/mL collagenase IV for about 5'–10 minutes at 37° C. Colonies are then harvested by removing individual colonies up with a Pipetman™ under a microscope or scraping, followed by gentle dissociation into small clusters in conditioned medium and then seeded onto matrix coated plates. Cells were seeded at a 1:3 or 1:6 ratio, approximately 90,000 to 170,000 cells $cm^{-2}$). Seeding dilution experiments indicated that the optimal minimum seeding density under these conditions is about 15,000 cells $cm^{-2}$.

Harvested hES cells were seeded onto Matrigel® or gelatin in mEF conditioned medium. The day after seeding, cells plated onto Matrigel® attached to the plate and formed small colonies that were less compact than hES colonies on feeder layers. Over the next few days, the colonies increased in size and the cells became more compact. The resulting culture contained very dense undifferentiated colonies surrounded by differentiated cells.

About one week after seeding the cultures became confluent and could be passaged. In contrast, cells seeded onto gelatin showed poor survival and the cells which survived appeared differentiated. Three hES cell lines, H1, H7 and H9 were cultured on Matrigel® in mEF conditioned medium. Cultures maintained under these conditions for over 100 days continued to display ES-like morphology.

The major components of Matrigel® are laminin, collagen IV and heparin sulfate proteoglycan. The ability of these components to support hES cell culture was tested separately. Laminin, collagen IV or fibronectin (all from Sigma) were diluted to a final concentration of 20 µg/mL, 10 µg/mL and 5 µg/mL in PBS, respectively.

The hES cells seeded onto laminin, fibronectin or collagen IV had colonies of undifferentiated hES cells, although the cultures on fibronectin or collagen IV did not contain as many undifferentiated colonies as the cultures on Matrigel® or laminin. When cells on Matrigel® or laminin reached confluence, the cells within the colonies became very compact, were morphologically very similar to the cells maintained on feeders and were serially passaged. After 40 days (6 passages), cells on Matrigel® and laminin contained a high proportion of colonies which continued to display ES-like morphology in long term culture. However, cells maintained on fibronectin or collagen IV had fewer colonies which displayed appropriate ES-morphology. As controls, cells cultured on Matrigel® or laminin in non-conditioned medium appeared to be proliferating more slowly and showed a differentiated morphology after a few passages.

FIG. 1 shows the morphology of hES cells in feeder-free culture. Panel A (Left Side) shows morphology of hES cells of the H1 line cultured on feeder cells in non-conditioned medium (mEF/RM), on Matrigel®, laminin, fibronectin, or collagen IV in mEF conditioned medium. Panel B shows morphology of hES cells of the H9 line maintained on Matrigel® in various types of conditioned medium, described in Example 7.

Laminins are major components of all basal laminae in vertebrates, which interact with integrin heterodimers, such as $\alpha1\beta1$, $\alpha2\beta1$, $\alpha3\beta1$, $\alpha6\beta1$ and $\alpha6\beta4$, on cell surface and mediate cell growth and migration during development. Among these integrins, $\alpha6\beta1$ and $\alpha6\beta4$ are specific for laminins; other integrins also interact with other matrices. Another experiment tested whether laminin receptors are expressed on hES cells and whether culturing hES cells on laminin or Matrigel® changes the expression of laminin receptors expression. Expression of integrins including $\alpha1$, $\alpha2$, $\alpha3$, $\alpha6$, $\beta1$ and $\beta4$ were examined by FACS analysis on cells maintained on feeders, or on Matrigel® or laminin in conditioned medium. For analyzing integrin expression, cells were stained with a panel of integrin specific antibodies by the laminin-specific integrins investigator kit (Chemicon International, Inc., Temecula, Calif.) and analyzed by FACS as described below.

FIG. 1 Panel C shows integrin expression measured in H1 hES cells maintained on feeders in non-conditioned medium (mEF/RM) or on Matrigel®, or on laminin in mEF conditioned medium (CM).

Cells maintained in Matrigel®/conditioned medium and laminin/conditioned medium were cryopreserved as follows: The cells were frozen in standard hES medium (not conditioned medium) supplemented with 10% DMSO and additional 10% SR (total 30%). The cells were thawed onto Matrigel® or laminin in conditioned medium. Cells maintained normal karyotype after being thawed.

Human ES cells maintained on Matrigel® in mEF conditioned medium showed a doubling time of about 31–33 hours, similar to the proliferation rate for hES cells grown on mEF feeder cells. H1 cells after 64 days of feeder-free culture showed a normal karyotype.

Example 4

Phenotypic Markers of hES Cells in Feeder-Free Culture

Undifferentiated hES cells express SSEA-4, Tra-1-60, Tra-1-81, OCT-4, and hTERT. The expression of these markers decreases upon differentiation. In order to assess whether the cells maintained in feeder-free conditions retained these markers, cells were evaluated by immunostaining, reverse transcriptase PCR amplification, and assay for telomerase activity.

Figure 2B:
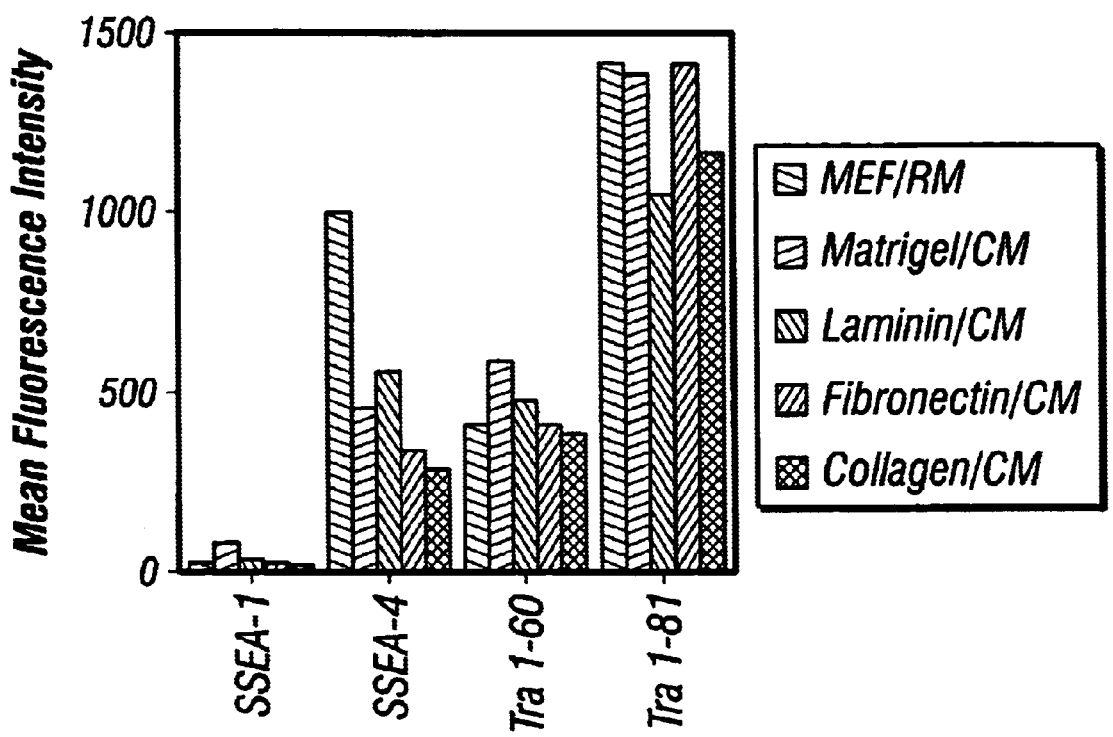
FIG. 2 shows surface marker expression in feeder-free cells by FACS analysis. Panel A is a FACS scan profile showing expression of SSEA-4, a glycoprotein expressed by hES cells grown on feeders in regular medium (mEF/RM), or on extracellular matrix with conditioned medium. Panel B is a bar graph showing fluorescence intensity of surface markers for hES cells cultured on different matrices. Panel C is a bar graph showing surface markers for hES cells cultured on Matrigel® in conditioned medium from different cell lines.

FIG. 2 shows surface marker expression in feeder-free cells by FACS analysis. Panel A: Expression of SSEA-4 in H1 cells maintained on feeders in non-conditioned medium (mEF/RM), on Matrigel®, laminin, fibronectin and collagen IV in mEF conditioned medium. Isotype controls are indicated by the dotted lines. Panel B. Mean fluorescence intensity of SSEA-1, SSEA-4, Tra-1-60 and Tra-1-81 in H1 cells cultured on different matrices. Panel C: Mean fluorescence intensity of SSEA-1, SSEA-4, Tra-1-60 and Tra-1-81 in H9 cells cultured on Matrigel® in conditioned medium from different cell lines.

For analysis by fluorescence-activated cell sorting (FACS), the hES cells were dissociated in 0.5 mM EDTA in PBS and resuspended to about $5\times10^5$ cells in 50 $\mu$L diluent containing 0.1% BSA in PBS. For analyzing surface marker expression, cells were incubated in the primary antibodies, including IgG isotype control (0.5 $\mu$g/test), IgM isotype control (1:10), SSEA-1 (1:10), SSEA-4 (1:20), Tra-1-60 (1:40) and Tra-1-81 (1:80), diluted in the diluent at 4° C. for 30 min. After washing with the diluent, cells were incubated with rat anti-mouse kappa chain antibodies conjugated with PE (Becton Dickinson, San Jose, Calif.) at 4° C. for 30 min. Cells were washed and analyzed on FACSCalibur™ Flow Cytometer (Becton Dickinson, San Jose, Calif.) using CellQuest™ software.

Similar to the hES cells on feeders, cells on Matrigel®, laminin, fibronectin or collagen IV expressed SSEA-4, Tra-1-60 and Tra-1-81. There was very little expression of SSEA-1, a glycolipid that is not expressed by undifferentiated hES cells.

FIG. 3 shows marker expression detected by histochemistry. For analysis by immunocytochemistry, cells were incubated with primary antibodies, including SSEA-1 (1:10), SSEA-4 (1:20), Tra-1-60 (1:40) and Tra-1-81 (1:80), diluted in knockout DMEM at 37° C. for 30 min. Cells were then washed with warm knockout DMEM and fixed in 2% paraformaldehyde for 15 min. After washing with PBS, cells were incubated with 5% goat serum in PBS at RT for 30 min, followed by incubation with the FITC-conjugated goat anti-mouse antibodies (1:125) (Sigma) at RT for 30 min. Cells were washed, stained with DAPI and mounted. The staining was typically performed 2 days after passaging. Cells were also examined for expression of alkaline phosphatase, a marker for undifferentiated ES cells. This was performed by culturing the cells on chamber slides, fixing with 4% paraformaldehyde for 15 min, and then washing with PBS. Cells were then incubated with alkaline phosphatase substrate (Vector Laboratories, Inc., Burlingame, Calif.) at room temperature in the dark for 1 h. Slides were rinsed for 2–5 min in 100% ethanol before mounting.

Figure 4:
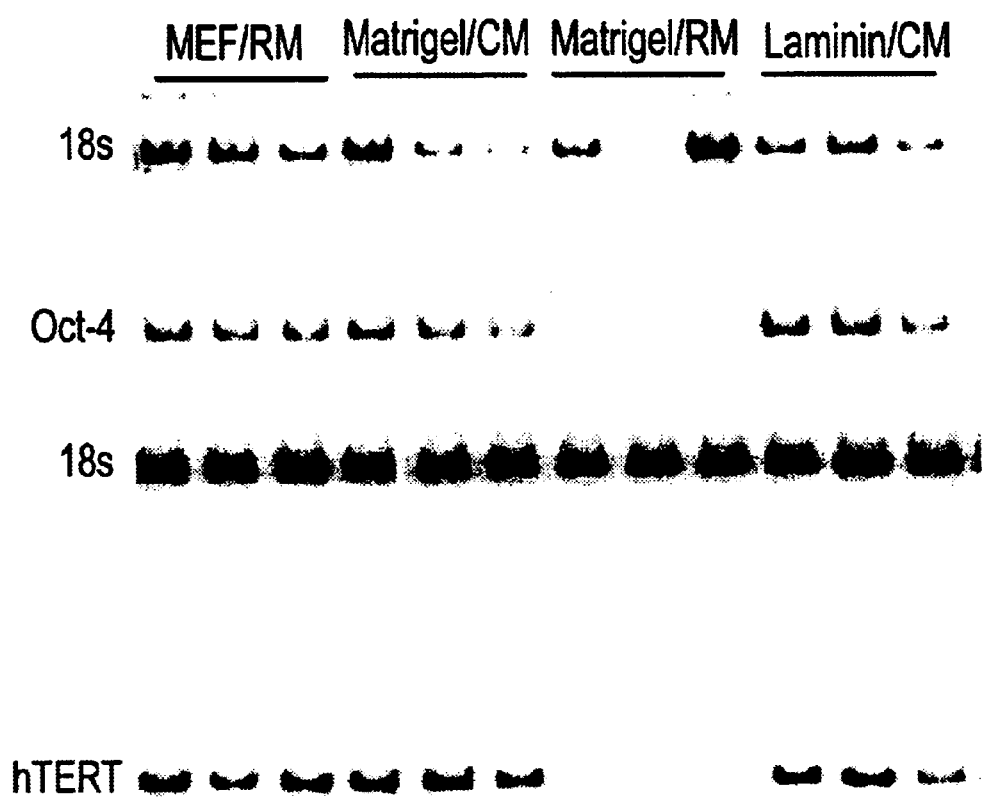
FIG. 4 provides an analysis of OCT-4 and hTERT expression in hES cells cultured with feeder cells (mEF) or extracellular matrix (Matrigel® or laminin) with regular medium (RM) or conditioned medium (CM). The upper panel is a copy of a gel showing OCT-4 and hTERT expression at the mRNA level by RT-PCR. The lower panel is a bar graph comparing the level of expression for cells grown on different substrates, expressed as the ratio of OCT-4 or hTERT to the 18s standard. hES cells grown on Laminin and Matrigel® in conditioned medium have similar expression patterns to those of cells grown on a feeder layer.

The results show that SSEA-4, Tra-1-60, Tra-1-81, and alkaline phosphatase were expressed by the hES colonies on Matrigel® or laminin, as seen for the cells on feeders—but not by the differentiated cells in between the colonies. FIG. 4 shows OCT-4 and hTERT expression of H1 cells on feeders and off feeders, as detected by reverse-transcriptase PCR amplification. For radioactive relative quantification of individual gene products, QuantumRNA™ Alternate 18S Internal Standard primers (Ambion, Austin Tex., USA) were employed according to the manufacturers instructions. Briefly, the linear range of amplification of a particular primer pair was determined, then coamplified with the appropriate mixture of alternate 18S primers:competimers to yield PCR products with coinciding linear ranges. Prior to addition of AmpliTaq™ (Roche) to PCR reactions, the enzyme was pre-incubated with the TaqStart™ antibody (ProMega) according to manufacturers instructions. Radioactive PCR reactions were analyzed on 5% non-denaturing polyacrylamide gels, dried, and exposed to phosphoimage screens (Molecular Dynamics) for 1 hour. Screens were scanned with a Molecular Dynamics Storm 860 and band intensities were quantified using ImageQuant™ software. Results are expressed as the ratio of radioactivity incorporated into the hTERT or OCT-4 band, standardized to the radioactivity incorporated into the 18s band.

Primers and amplification conditions for particular markers are as follows. OCT-4: Sense (SEQ. ID NO:3) 5'-CTTGCTGCAG AAGTGGGTGG AGGAA-3' AntiSense (SEQ. ID NO:4) 5'-CTGCAGTGTG GGTTTCGGGC A-3'; alternate 18: competimers 1:4; 19 cycles (94° 30 sec; 60° 30 sec; 72° 30 sec). hTERT: Sense (SEQ. ID NO:5) 5'-CGGAAGAGTG TCTGGAGCAA-3' AntiSense (SEQ. ID NO:6) 5'-GGATGAAGCG GAGTCTGGA-3'; alternate 18: competimers 1:12; 34 cycles (94° 30 sec; 60° 30 sec; 72° 30 sec).

The transcription factor OCT-4 is normally expressed in the undifferentiated hES cells and is down-regulated upon differentiation. In this experiment, it was found that the cells maintained on Matrigel® or laminin in conditioned medium (CM) for 21 days express OCT-4, whereas cells maintained in Matrigel® g in unconditioned regular medium (RM) did not. Cells maintained on fibronectin or collagen IV, which showed a large degree of differentiation, expressed lower levels of OCT-4 compared to cells on feeders, Matrigel® or laminin.

hTERT and OCT-4 expression was seen in all the culture conditions except Matrigel® and regular medium. Furthermore, after exposure of cells to retinoic acid (RA) or dimethyl sulfoxide (DMSO), factors that promote cell differentiation, the expression of hTERT was markedly decreased.

Figure 5:
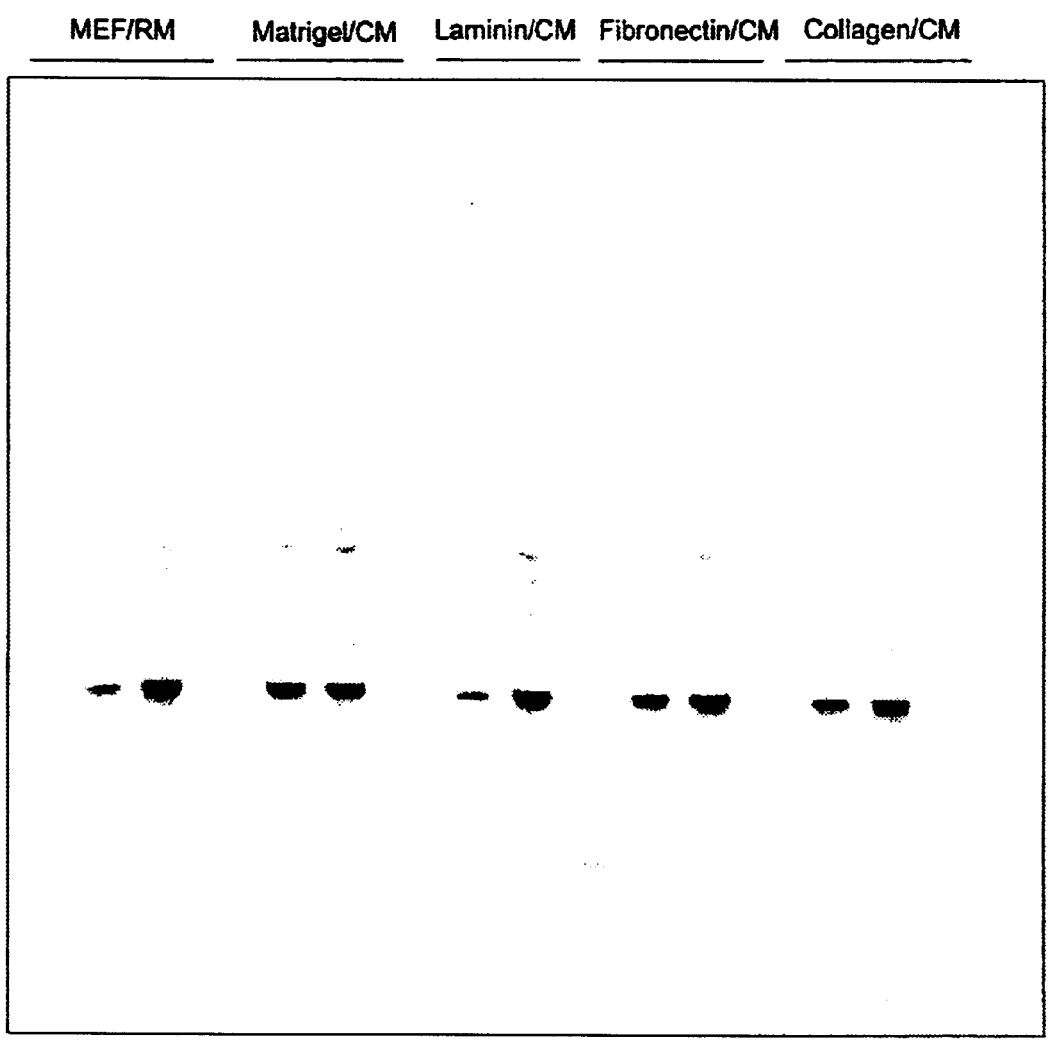
FIG. 5 is a half-tone reproduction of a gel showing telomerase activity measured in cultured hES cells by TRAP activity assay. All the cultures conditions showed positive telomerase activity after 40 days in feeder-free culture.

FIG. 5 shows telomerase activity measured by TRAP activity assay (Kim et al., Science 266:2011, 1997; Weinrich et al., Nature Genetics 17:498, 1997). All the cultures conditions showed positive telomerase activity after 40 days on Matrigel®, laminin, fibronectin or collagen IV in mEF conditioned medium.

Example 5

In Vitro and In Vivo Differentiation

This experiment evaluated the capacity of hES cells to differentiate into cell types of different lineages.

In vitro differentiation was induced in H1 hES cells maintained in conditioned medium on Matrigel®, laminin, fibronectin or collagen IV for 26 days. The hES cells were dissociated into small clumps by incubating in ~200 U/mL collagenase IV at 37° C. for 10 min, and cultured in suspension to form embryoid bodies (EBs) in medium containing DMEM, 20% FBS (Hyclone), 1 mM glutamine, 0.1 mM β-mercaptoethanol, and 1% non-essential amino acids (Gibco). After 4 days in suspension, the aggregates were transferred onto polyornithine-coated plates, and cultured for additional 7 days. The cultures were then examined for the presence of beating cells, and processed for immunohistochemistry.

Figure 6:
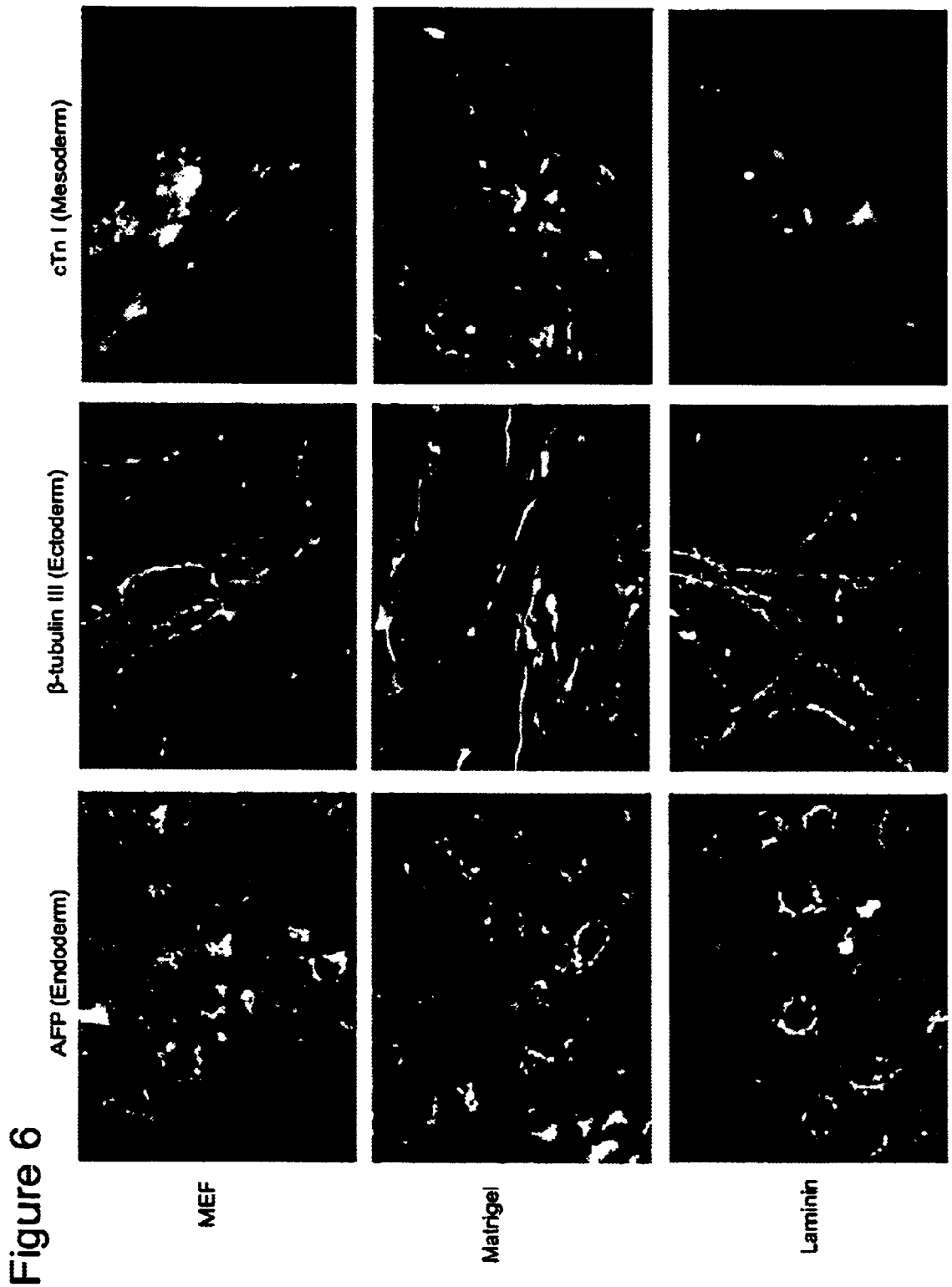
FIG. 6 is a half-tone reproduction of immunohistochemistry performed on cultured hES cells that were allowed to differentiate through embryoid body formation. Regardless of whether the hES had been cultured on feeders or on extracellular matrix, the staining patterns are consistent with a potential for differentiation into different cell types. The staining patterns show cells of the neuron and cardiomyocyte lineages (β-tubulin III and cardiac troponin I, respectively. There are also cells staining for α-fetoprotein, a marker of endoderm lineage.

FIG. 6 shows results of immunocytochemical analysis of these cells. The staining patterns were consistent with cells of the neuron and cardiomyocyte lineages (β-tubulin III and cardiac troponin I, respectively). About 8 days after differentiation, beating regions were identified in all cultures. There were also cells staining for α-fetoprotein, a marker of endoderm lineage.

hES cells were also tested for their ability to form teratomas by intramuscular injection into SCID mice. Cells maintained on feeders or off feeders were harvested, resuspended in PBS and injected intramuscularly into SCID/beige mice ($5 \times 10^6$ cells per site). Tumors were excised and processed for histological analysis. The hES cells from feeder-free culture generated tumors, which were excised and processed for histological analysis after 78–84 days.

Figure 7:
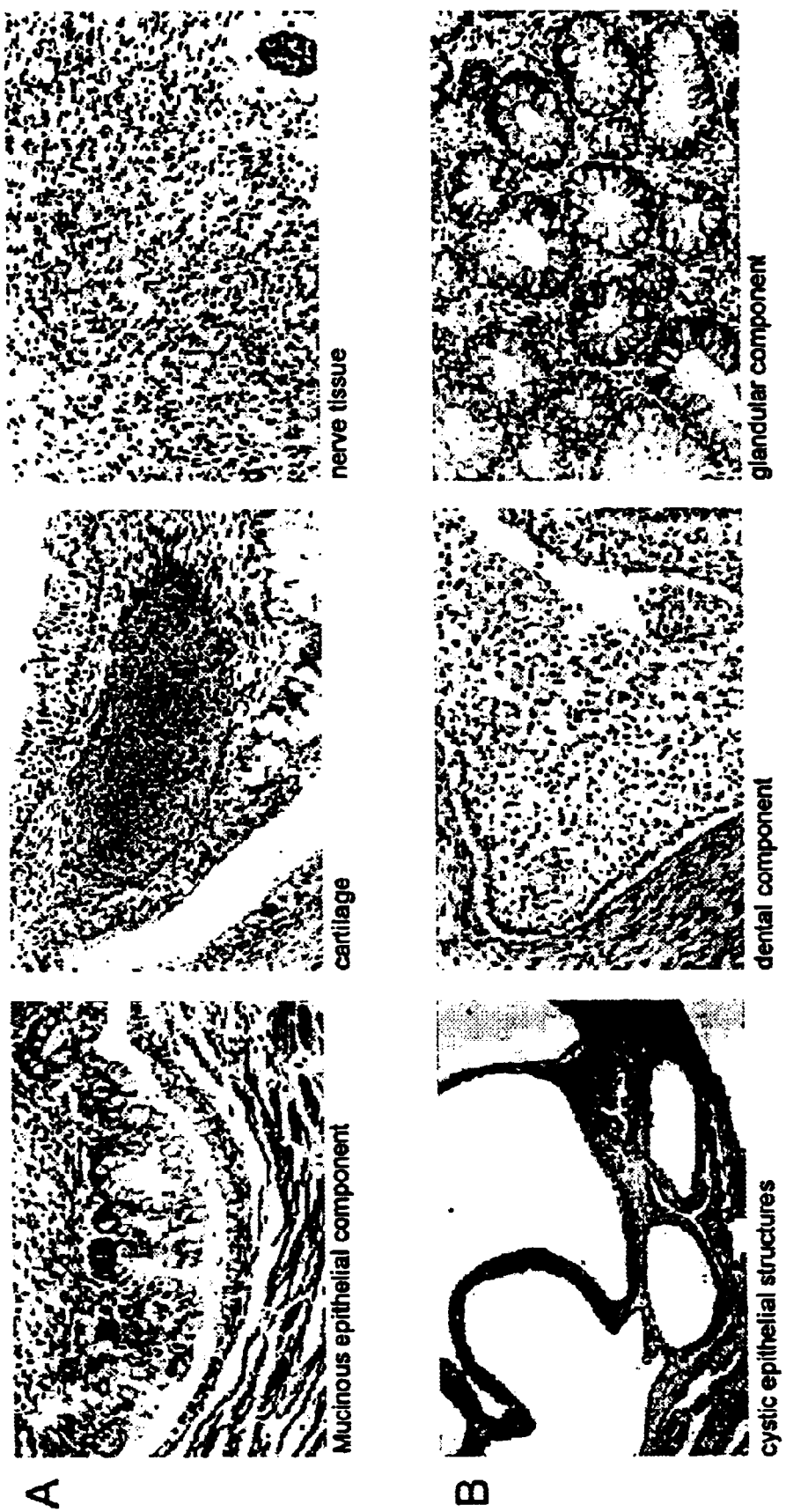
FIG. 7 is a half-tone reproduction of the histopathology of teratomas derived from hES cells, as another indicator of their ability to differentiate into different cell lineages. Panel A (Upper Row) shows a number of different cells in teratomas from hES grown on mEF feeder cells. Panel B (Lower Row) shows different cells in teratomas from hES grown in feeder-free culture.

FIG. 7 shows the histopathology of teratomas derived from H7 cells maintained with mEF feeder cells (A), or in feeder-free culture (B). Mucinous epithelial component, cartilage and nerve tissue were observed in teratomas derived form hES cells cultured on feeders. Cystic epithelial structures, probable dental component, cartilage and glandular epithelial or neural components were found in teratomas derived from feeder-free hES cultures.

Example 6

Preparation of The Immortalized Feeder Cell Line NH190

In this example, a permanent mouse cell line was established that is suitable for conditioning medium for the culture of primate pluripotent stem (pPS) cells. The NHG190 line is a mouse embryonic fibroblast cell line immortalized with telomerase that is triple drug resistant, and expresses green fluorescent protein (GFP).

Two mouse strains were obtained from Jackson Laboratory (Bar Harbor, Me.) that have a transgene for resistance to the antibiotics neomycin or hygromycin. The C57BL/6J TgN(pPGKneobpA)3 Ems mice and C57BL/6J-TgN (pPWL512hyg)1Ems mice from Jackson Labs were crossbred. Embryos that were both neomycin- and hygromycin-resistant were dissected at day 13.5 post conception according to standard protocols for preparing mouse embryonic fibroblasts (mEF) for feeder layers (E. J. Robertson, pp. 71–112 in *Teratocarcinoma and Embryonic Stem Cell Lines*, ed. E. J. Robertson, Oxford: IRL Press, 1987). The derived mEF cells were stored frozen.

The mEFs were thawed in growth medium containing 20% fetal calf serum (HyClone), 2 mM L-glutamine (Gibco/BRL), 80% DMEM (Gibco/BRL). The cells were expanded using 1:2 split ratios for 4 passages. Two flasks that had reached ~75% confluence were fed with fresh medium 4 h prior to electroporation. Cells were removed from the flasks with 0.5% trypsin/500 mM EDTA (Gibco/BRL), pelleted at 400×g for 5 min at room temperature, and resuspended in the growth medium at a concentration of $4 \times 10^6$ cells/mL.

The cell suspension was divided into two 500 μL aliquots and transferred to two 0.4 cm gap electroporation cuvettes (BioRad). One cuvette received 5 μg of the control plasmid (pBS212; puromycin-resistance gene driven by the SV40 early enhancer/promoter); the other received 5 μg of pGRN190, comprising the murine telomerase reverse transcriptase (mTERT) coding region driven by MPSV promoter plus puromycin resistance gene driven by the SV40 early enhancer/promoter. The cells and DNA were mixed by hand, and electroporated using a BioRad gene Pulser with a BioRad capacitance extender at a setting of 300V, 960 μF.

Each aliquot of cells was transferred to an individual 150 cm plate containing 25 mL of growth medium. The medium on the plates was exchanged on the following day, and on the next day, growth medium was replaced by growth medium plus 0.5 μg/mL puromycin. The medium on the plates was exchanged for fresh puromycin-containing medium every 48 hrs until 29 days after electroporation. At this time, large individual colonies of puromycin-resistant cells were evident in both the pBS212-and pGRN190-electroporated plates. Ten colonies from the control plate and 12 from the pGRN190-electroporated plate were isolated with cloning cylinders and each colony was transferred to 1 well of a 48-well plate (1 well per colony).

One week later, all surviving colonies that had expanded to reach confluence in the 48 well plate (three control colonies, 1 pGRN190-electroporated colony) were transferred individually to wells of a 24 well plate. Six days later, the only colony that had continued to expand was derived from the pGRN190-electroporated plate, and was subsequently designated NH190. The cells were maintained in growth medium plus 0.5 µg/mL puromycin. Analysis for telomerase activity by TRAP assay (Kim et al., Nucleic Acids Res. 25:2595, 1997) demonstrated that NH190 cells express functional telomerase activity.

To facilitate monitoring of the cells in mixed culture populations and in vivo, NH190 cells were further infected with a retroviral construct conferring expression of green fluorescent protein (GFP). The enhanced GFP sequence from plasmid pEGFP-1 is one of the Living Colors™ fluorescent protein vectors, available from ClonTech. It contains an enhanced GFP encoding region, with changes that alter restriction nuclease cleavage sites, and shift the excitation and emission wavelengths of the encoded protein. The EGFP-1 sequence was cloned into the vector pMSCV.neo, ClonTech cat # K1062–1. NH190 cells were transduced with the engineered vector, and GFP positive cells were separated by FACS sorting. The GFP expressing cell line was designated NHG190. These cells have been carried in culture for over 3 months.

Example 7

Alternative Sources of Conditioned Medium

Conditioned medium from several cell lines were tested, including medium from mEF (primary mouse embryonic fibroblasts), STO (immortal mouse embryonic fibroblast cell line), NHG190 (Example 6), BJ (human foreskin fibroblast cell line immortalized with telomerase), and RPE (human retinal epithelial cell line immortalized with telomerase).

Medium used for growing cells was as follows. 1. mEF medium: 90% DMEM (Gibco BRL, Rockville, Md.), 10% fetal bovine serum (FBS) (heat inactivated) (Hyclone), and 2 mM L-glutamine. 2. STO medium: mEF medium supplemented with 0.1 mM non-essential amino acids. 3. BJ 5ta medium: 90% DMEM and 10% Cosmic calf serum (not heat inactivated). 3. NHG190 medium: mEF medium supplemented with additional 10% FBS. 4. RPE medium: 90% DMEM/F12, 10% FBS (not heat inactivated), 10 ml L-glutamine and 3.48 g/L sodium bicarbonate. 5. Differentiation medium: 80% knockout Dulbecco's modified Eagles medium (KODMEM), 1 mM L-glutamine, 0.1 mM β-mercaptoethanol and 1% nonessential amino acids, supplemented with 20% FBS.

To prepare conditioned medium, the respective cell lines were harvested by washing once with $Ca^{++}/Mg^{++}$ free PBS, incubating in trypsin/EDTA (Gibco) for about 5 min, and suspending in mEF medium. The cells were irradiated at ~4000 rad (~508 sec at 140 kV: shelf setting 6 in a Torrex generator, EG&G Astrophysics Research Corp., Long Beach Calif.). They were then counted, and seeded at ~55,000 cells/$cm^2$ for mEFs, ~38,000/$cm^2$ for NHG190 cells, ~95,000/$cm^2$ for STO cells, ~80,000/$cm^2$ for BJ cells, ~90,000/$cm^2$ for RPE cells. After at least 4 h, the medium was exchanged with ES medium containing 4 ng/mL bFGF. Conditioned medium was collected daily thereafter, and used for feeding of hES cultures. Before addition to the hES cultures, each conditioned medium was supplemented with 4 ng/mL of human basic fibroblast growth factor (hbFGF; Gibco).

FIG. 1, Panel B (Right Side) shows morphology of hES cells of the H9 line maintained on Matrigel® in medium conditioned by mEF, NHG190, STO and BJ, compared with unconditioned regular medium (RM). The cells in RPE conditioned medium differentiated within the first week of culture. The cells in the other conditioned mediums all had hES colonies with appropriate ES-morphology. Based on the morphology, confluence of the culture, and the ratio of differentiated to undifferentiated cells the conditioned medium can be ranked in order of decreasing preference as follows: primary mEF, NHG190, STO, and BJ.

Figure 2C:
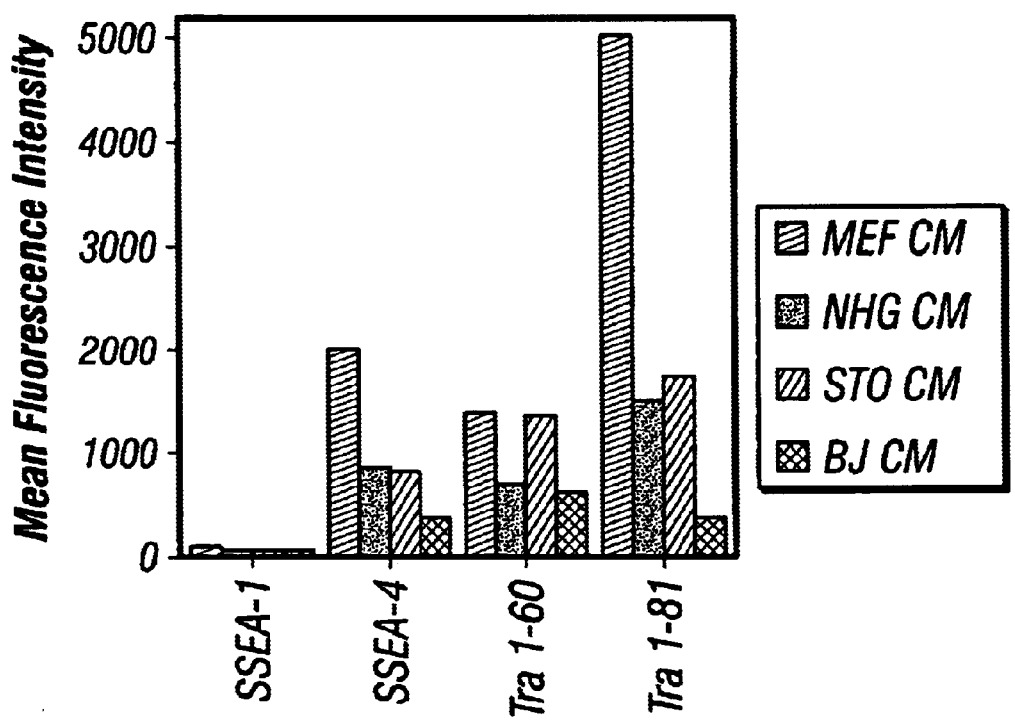

Similar to cells maintained in conditioned medium from primary mEF, cells on Matrigel® or laminin in medium conditioned by other cell lines, including NHG190, STO and BJ, expressed high levels of SSEA-4, Tra-1-60 and Tra-1-81 but low levels of SSEA-1 as analyzed by FACS analysis (FIG. 2C). Cells on Matrigel® or laminin in mEF conditioned medium or NHG190 conditioned medium were able to differentiate into three germ layer cell types. Immunocytochemical analysis of the differentiated cultures showed positive staining for β-tubulin III consistent with neurons (ectoderm lineage), cardiac troponin I consistent with cardiomyocytes (mesoderm lineage), and α-fetoprotein, consistent with cells of the endoderm lineage.

In Examples 1–3, medium was prepared by adding 4 ng/mL hbFGF to the medium before conditioning with the mEFs, and then again when the conditioned medium was collected and used for feeding of the hES cells. To determine if both additions of hbFGF to the medium are necessary to maintain the ES cells in the undifferentiated state, experiments were performed in which one or both additions of hbFGF were eliminated.

Cultures maintained in conditioned medium without the second addition of hbFGF did not appear healthy at early passages, and appeared differentiated after 29 days in culture. Cells maintained in conditioned medium without the first addition of hbFGF displayed mostly differentiated morphology, but still formed smaller undifferentiated colonies after 27 days in culture. Cells maintained in conditioned medium without either addition of hbFGF completely differentiated after 18 days. In contrast, cells cultured in conditioned medium prepared with both additions of bFGF appeared healthy and undifferentiated in long-term culture. Thus, preparing conditioned medium by adding bFGF both before and after culturing with the feeder cells helps prevent differentiation of hES cells in the subsequent feeder-free culture.

Storage of conditioned medium was tested as follows: Batch medium was prepared by conditioning for 1–2 days in mEF cell cultures as described, and stored at 4° C. in sealed culture flasks. Feeder-free hES cell cultures were maintained with stored medium exchanged daily. Characteristic morphological features of undifferentiated stem cells were still present after at least 7 days, comparable to hES cells maintained in freshly conditioned medium.

To determine if leukemia inhibitory factor (LIF) can substitute for conditioned medium in maintaining hES cells without feeders, cells of the H1 and H9 line were cultured on Matrigel® in ES medium containing LIF at a final concentration of 1500, 1,000, or 500 U/mL (recombinant LIF from R&D systems; Catalog # 250-L). Cells were simultaneously cultured in mEF conditioned medium as the positive control, and unconditioned ES medium as negative control. After one week, cultures in medium either with or without LIF showed a large degree of differentiation, while cultures maintained in mEF conditioned medium contained predominately undifferentiated colonies. These data indicate that LIF will not maintain hES cells in an undifferentiated state in the absence of feeder cells.

Example 8

Isolation of mRNA for Producing cDNA Libraries

In this example, poly A+ mRNA was isolated from undifferentiated and differentiated pPS cells according to standard methodology.

Human embryonic stem cells were obtained either from cultures grown on feeder cells, or in a feeder-free environment, as described elsewhere in this disclosure. cDNA libraries have been obtained from both. Using feeder-free cultures has the advantage of producing libraries that are free of contaminating mouse RNA, and can be more easily scaled to produce large numbers of cells for mRNA isolation.

Total RNA was isolated from hES cells using the RNeasy™ protocol and reagents (Qiagen, Germany) according to manufacturers directions. Briefly, cells were lysed directly in the culture dish using a solution of guanidinium isothiocyanate (GITC) and the resulting extract was bound to the RNeasy™ matrix under conditions in which RNA is bound, but contaminants and genomic DNA are not. After washing the matrix with the prescribed buffers supplied by the manufacturer, the total RNA was eluted with water and quantified by absorbance at 260 nm.

Poly A+ mRNA was then purified from the total RNA preparation by using the Oligotex™ protocol and reagents (Qiagen, Germany). Briefly, bead matrices containing covalently bound $dC_{10}T_{30}$ oligonucleotides were mixed with total RNA, allowing interaction between the polyA+ tails of mRNAs with the $dC_{10}T_{30}$-bound beads. After washing with specified wash solutions, the bound mRNA was released in a low salt buffer, and the yield was quantified by absorbance at 260 nm. Gel electrophoresis confirmed the overall purity of the poly A+ mRNA.

cDNA synthesis was accomplished using a standard protocol (SuperScript™ Lambda System, Life Technologies, Rockville, Md.). One μg of poly A+ mRNA was converted to single-stranded cDNA using an oligo dT-NotI primer/adaptor and SuperScript™ II reverse transcriptase. [$^{32}$P] dCTP was included in the reaction to allow for the calculation of the first strand conversion efficiency. The single stranded cDNA was then converted into double stranded cDNA using DNA polymerase in the presence of DNA ligase and RNaseH (all enzymes of E. coli origin). The double-stranded cDNA was ligated with SalI adaptors and then resolved by gel exclusion chromatography. A portion of each column fraction was analyzed by gel electrophoresis, and fractions containing cDNA with a predicted median size of 2 kbp or larger were pooled. The size-selected cDNA pool was then restricted with NotI endonuclease, and ligated with NotI/SalI-restricted pSportl plasmid (Life Technologies). The ligation products were used to transform UltraMax™ competent E. coli (Life Technologies), which were subsequently plated onto medium plates containing ampicillin. Libraries produced by these methods typically consisted of $5 \times 10^6$ or more independent clones with a median cDNA insert size of ~1.2 kbp, as judged by PCR of plasmid preparations from individual colonies.

cDNA libraries have also been prepared from embryoid body (EB) cells, which comprise a mixed population of cells differentiated from hES cells. To prepare EBs, monolayer cultures of hES cells were harvested by incubating with ~200 U/mL collagenase IV for ~5–20 min at 37° C. The hES cells were dissociated into clusters and plated in non-adherent cell culture plates (Costar) in Differentiation Medium, composed of 80% KO DMEM (Gibco), 20% non-heat-inactivated FBS (Hyclone), 1% non-essential amino acids, 1 mM glutamine, and 0.1 mM β-mercaptoethanol.

The EB were then seeded at a 1:2 ratio in 2 mL medium per 9.6 $cm^2$ well. The EBs were fed every other day by adding 2 mL of medium per well up to 4 mL/well, and then collecting and resuspending in 2 mL fresh medium. Total RNA was prepared after ~2–8 days in suspension culture. Alternatively, EBs were maintained in suspension culture for ~4 days, and then plated onto gelatin coated plates and cultured for a further 7 days. This results in formation of a diverse cell population, and improves the yield of RNA, probably because of higher cell density. Yield of total RNA from ~20 to $500 \times 10^6$ cells was ~25 to 2500 μg.

Example 9

Selection of Promoters For cDNA Expression In Embryonic Stem Cells

A variety of promoters were tested for their ability to drive stable long-term gene expression in undifferentiated hES cells. Constructs were introduced either by retroviral transduction, or by FuGENE™ mediated lipofection.

hES cells plated in 6 well plates were removed from the feeder layer with collagenase (~200 units/mL) at 37° for 7–10 min. When colonies began to detach, the collagenase from each well was aspirated and replaced with 2 mL of standard hES growth medium/well. The hES cells were removed by scraping the surface of a single well with a 5 mL pipet and transferred to a 50 mL conical tube. Additional hES growth medium was added to a final volume of 10 mL. The cell suspension was triturated 10–12 times with a 10 mL pipet, and an additional 8 mL of standard hES growth medium added. Three mL of the cell suspension were added to each well of 6 well plates that were pre-coated with gelatin and mEF feeder layers as described above (i.e., 1 well of a 6 well plate was sufficient to seed 6 wells of a new plate).

Transduction using retrovirus was conducted as follows. Retroviral vector designated GRN354 was constructed at Geron Corp. using PMSCVneo vector purchased from ClonTech (cat # K1062-1). The eGFP encoding region was inserted downstream from the MSCV LTR. The LTR drives expression of GFP and the vector also contains the $neo^r$ gene driven by the murine PGK promoter.

Plates were coated with 0.5% gelatin and NHG190 feeder cells ($7.5 \times 10^4$ in 1 mL NHG190 medium for 24 well plates; $3.75 \times 10^5$ in 3 mL medium for 6 well plates). The hES line H7 was seeded onto a 24 well prepared plate in hES medium (1 mL/well). Forty-eight h later, 3 wells of hES cells were detached using 0.05% trypsin/5 mM EDTA (Sigma) at 37° C., resuspended in 500 μL NHG190 medium, and counted. Stock of retrovirus construct pGRN354 was thawed on ice immediately prior to use. Growth medium was aspirated from the wells and replaced with 400 μL hES medium plus 8 μL retrovirus (MOI of 10) and 4 μL of 8 mg/mL polybrene solution (Sigma). Two h later, 800 μL hES growth medium were added per well. Each transduced well was refed with 1 mL fresh hES medium every 24 h.

Four days after transduction, medium was replaced with 1 mL hES growth medium containing 200 μg/mL geneticin. After 3 days of geneticin selection, the cells were detached with collagenase, triturated, resuspended in 3 mL hES medium, reseeded into one well of a 6-well plate coated with gelatin and NHG 190 feeders, and refed with hES medium after 24 h. The medium was then again replaced with hES medium containing geneticin and refed every 24 h.

Lipofection using FuGENE™ 6 (Roche) was conducted according to manufacturers directions. The plasmid DNA (5–10 μg of pEGFP-C1, ClonTech cat. # 6084–1) was diluted in water to a final volume of 100 μl. In pilot experiments, 5–30 μL of FUGENE™ were added to sufficient OptiMEM™ solution (Gibco, cat # 11-58-021) to achieve a final volume of 100 μL. The DNA solution was then added slowly to the FuGENE™ solution and mixed gently. The mixture was incubated at room temperature for 30 min before being supplemented with 800 μL of Opti-MEM™.

Forty-eight hours prior to transfection, hES cells were seeded onto 6 well plates that had been coated with gelatin and mEF feeder layers. Cells were washed with 3 mL of pre-warmed OptiMEM™ and incubated in DNA/lipid mixture solution at 37° C. for 4 h. In some experiments, after 4 h the wells received an additional 2 mL of mEF-conditioned medium; in others the DNA/lipid mixture was added to wells containing 2 mL of mEF-conditioned medium and the cells were incubated in this mixture overnight.

In subsequent experiments, feeder-free cultures of hES cells were transfected using FuGENE™. In these experiments, undifferentiated hES cells were seeded onto Matrigel®-coated 6-well plates (at a typical density of ~1.5×10$^4$ cells cm$^{-2}$) in mEF conditioned medium plus an additional 4 ng/mL hbFGF. Forty-eight h after plating, the cells were transfected with FuGENE™ as already described. Forty-eight h after transfection, cells were re-fed with mEF conditioned medium plus 4 ng/mL hbFGF and 200 μG/mL geneticin. Subsequently, the cells were re-fed with medium containing 200 μG/mL geneticin on a daily basis. Results of representative experiments are summarized in Table 2.

TABLE 2

Testing of Promoters for Expression in human Embryonic Stem Cells

| Method | Constructs (promoter/ORF combination) | Number of Undifferentiated Lines Derived | Result |
| --- | --- | --- | --- |
| Retrovirus Transduction | MSCV-LTR/GFP; PGK/neo (single vector) | mixed culture | 100% G418 resistant 50–65% GFP positive |
| Lipofection | CMV/β-galactosidase; SV/neo (single vector) | 3 | 100% G418 resistant β-galactosidase negative |
| Lipofection | CMV/GFP; PGK/neo (2 vectors cotransfected) | 5–6 pooled colonies | 100% G418 resistant GFP negative |
| Lipofection | UbiC*/β-galactosidase; PGK/neo (2 vectors cotransfected) | 1 | 100% G418 resistant β-galactosidase negative |
| Lipofection | EF1α/β-galactosidase; PGK/neo (2 vectors cotransfected) | 13 individual lines, 4–5 pooled colonies | 100% G418 resistant GFP negative |
| Lipofection | MSCV LTR/neo; PGK/ηTERT (single vector) | 0 | 100% G418 resistant differentiated cells only |

Based on these results, the PGK promoter was selected to drive stable long-term expression of cDNA clones in undifferentiated hES cells.

It will be recognized that the compositions and procedures provided in the description can be effectively modified by those skilled in the art without departing from the spirit of the invention embodied in the claims that follow.

What is claimed as the invention is:

1. A method of obtaining an mRNA preparation or a cDNA library from undifferentiated primate pluripotent stem (pPS) cells or their differentiated progeny, comprising:
   a) providing undifferentiated pPS cells cultured in a suitable nutrient medium on an extracellular matrix but essentially free of feeder cells,
   b) optionally permitting the pPS cells to differentiate, and
   c) isolating mRNA from the undifferentiated or differentiated cells.

2. The method of claim 1, which is a method for obtaining mRNA from undifferentiated pPS cells, comprising isolating mRNA from pPS cells in a culture essentially free of feeder cells.

3. The method of claim 1, which is a method for obtaining a cDNA library from undifferentiated pPS cells, comprising isolating mRNA from pPS cells in a culture essentially free of feeder cells, and recombining cDNA copies of the mRNA into a cloning vector.

4. The method of claim 3, wherein the cloning vector is an expression vector in which cDNA is operatively linked to a transcriptional regulatory control element that promotes transcription of the cDNA in undifferentiated pPS cells.

5. The method of claim 4, wherein the regulatory control element is a phosphoglycerate kinase (PGK) promoter.

6. The method of claim 1, wherein the culture of pPS cells essentially free of feeder cells has been maintained in a culture environment comprising an extracellular matrix, and a nutrient medium conditioned by culturing feeder cells in the medium, and then harvesting the medium for use in culturing the pPS cells.

7. The method of claim 6, wherein the feeder cells are a euploid human cell line that can be maintained in culture for at least 60 days.

8. The method of claim 1, wherein the pPS cells are human embryonic stem (hES) cells.

9. The method of claim 1, which is a method for obtaining mRNA from differentiated cells, comprising obtaining pPS cells from a culture essentially free of feeder cells, permitting the pPS cells to differentiate, and isolating mRNA from the differentiated cells.

10. The method of claim 1, which is a method for obtaining a cDNA library from differentiated cells, comprising isolating mRNA from cells differentiated from pPS cells obtained from a culture essentially free of feeder cells, and recombining cDNA copies of the mRNA into a cloning vector.

11. The method of claim 1, which is a method for obtaining a cDNA library enriched for transcripts differently expressed upon differentiation of pPS cells, comprising incubating together preparations of mRNA (or cDNA copies thereof) obtained from undifferentiated pPS cells in feeder-free culture, and from cells differentiated from pPS cells, under conditions that permit polynucleotides present from each preparation to cross-hybridize; and then recombining polynucleotides that have not cross-hybridized into a cloning vector.

12. A cDNA subtraction library enriched for transcripts that alter expression during differentiation, produced according to the method of claim 11.

13. The method of claim 1, which is a method for obtaining a cDNA library enriched for transcripts differently expressed in two differentiated cell types, comprising differentiating pPS cells from feeder-free culture into two differentiated cell types; incubating together preparations of mRNA (or cDNA copies thereof) obtained from the two cell types under conditions that permit polynucleotides present from each preparation to cross-hybridize; and then recombining polynucleotides that have not cross-hybridized into a cloning vector.

14. The method of claim 1, which is a method for obtaining a cDNA library enriched for transcripts that undergo altered expression as a consequence of exposure to a compound, comprising incubating together two preparations of mRNA (or cDNA copies thereof) obtained from pPS cells in feeder-free culture under conditions that permit polynucleotides present from each preparation to cross-hybridize, wherein the first preparation is from pPS cells that have been exposed to the compound and the second preparation is from pPS that have not been exposed to the compound; and then recombining polynucleotides that have not cross-hybridized into a cloning vector.

15. A cDNA library of undifferentiated primate pluripotent stem (pPS) cells, which can be obtained by providing undifferentiated pPS cells cultured in a suitable nutrient medium on an extracellular matrix but essentially free of feeder cells, and isolating mRNA from the undifferentiated cells.

16. A host cell containing the cDNA library of claim 15.

17. A cDNA library comprising cDNA from at least 1,000 genes expressed at the mRNA level, wherein the library has been obtained from undifferentiated pPS cells, and is essentially free of cDNA of other vertebrates.

18. The cDNA library of claim 17, cloned in an expression vector in which cDNA is operatively linked to a transcriptional regulatory control element that promotes transcription of the cDNA in undifferentiated pPS cells.

19. The cDNA library of claim 18, wherein the regulatory control element is a phosphoglycerate kinase (PGK) promoter.

20. The DNA library of claim 17, wherein at least 30% of cDNA segments in the library comprise the entire encoding region of the corresponding mRNA.

21. The cDNA library of claim 17, wherein the pPS cells are human embryionic stem (hES) cells. kinase (PGK) promoter.

22. A host cell containing the cDNA library of claim 17.

23. A cDNA library of at least 1,000 genes in which at least 50% of the cDNA is from genes that are modulated during differentiation of pPS cells, essentially free of cDNA of other vertebrates.

24. The cDNA library of claim 23 enriched for transcripts that alter expression while forming embryoid bodies from hES cells.

25. A method for producing a polynucleotide containing a sequence of an mRNA expressed in undifferentiated or differentiated pPS cells, comprising:
   a) obtaining the cDNA library of claim 15,
   b) determining nucleotide sequence from a cDNA contained in the library; and
   c) manufacturing a polynucleotide containing the determined sequence.

26. A method for producing a polynucleotide containing a sequence of an mRNA expressed in undifferentiated or differentiated pPS cells, comprising determining nucleotide sequence from an mRNA or cDNA obtained according to claim 1, and manufacturing a polynucleotide containing the determined sequence, wherein the mRNA is upregulated or downregulated when pPS cells differentiate.

27. A method for producing a polynucleotide containing a sequence of an mRNA expressed in undifferentiated pPS cells, comprising determining nucleotide sequence of a cDNA in the cDNA library of claim 17, and manufacturing a polynucleotide containing the determined sequence.

* * * * *

SEQUENCE LISTING

<160> NUMBER OF SEQ ID NOS: 6

<210> SEQ ID NO 1
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 1
aggtcgacga gagag                                                        15

<210> SEQ ID NO 2

```
<211> LENGTH: 15
<212> TYPE: DNA
<213> ORGANISM: Artificial Sequence
<220> FEATURE:
<223> OTHER INFORMATION: Description of Artificial Sequence:   Primer

<400> SEQUENCE: 2
ctctctcgtc gacct                                                          15

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence:   Primer

<400> SEQUENCE: 3
cttgctgcag aagtgggtgg aggaa                                               25

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence:   Primer

<400> SEQUENCE: 4
ctgcagtgtg ggtttcgggc a                                                   21

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:   Primer

<400> SEQUENCE: 5
cggaagagtg tctggagcaa                                                     20

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence:   Primer

<400> SEQUENCE: 6
ggatgaagcg gagtctgga                                                      19
```